United States Patent
Sangaralingham et al.

(10) Patent No.: US 9,857,382 B2
(45) Date of Patent: Jan. 2, 2018

(54) ASSESSING RENAL STRUCTURAL ALTERATIONS AND OUTCOMES

(71) Applicant: Mayo Foundation for Medical Education and Research, Rochester, MN (US)

(72) Inventors: Sasantha J. Sangaralingham, Rochester, MN (US); John C. Burnett, Jr., Rochester, MN (US); Alessandro Cataliotti, Rochester, MN (US); Denise M. Heublein, Altura, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 15/078,835

(22) Filed: Mar. 23, 2016

(65) Prior Publication Data

US 2016/0252528 A1 Sep. 1, 2016

Related U.S. Application Data

(63) Continuation of application No. 14/367,185, filed as application No. PCT/US2012/059670 on Oct. 11, 2012, now abandoned.

(60) Provisional application No. 61/580,139, filed on Dec. 23, 2011.

(51) Int. Cl.
| | |
|---|---|
| A61K 38/00 | (2006.01) |
| C07K 7/14 | (2006.01) |
| A61K 38/22 | (2006.01) |
| G01N 33/68 | (2006.01) |
| C07K 14/58 | (2006.01) |
| A61K 45/06 | (2006.01) |

(52) U.S. Cl.
CPC ..... *G01N 33/6893* (2013.01); *A61K 38/2242* (2013.01); *A61K 45/06* (2013.01); *C07K 14/58* (2013.01); *G01N 2333/58* (2013.01); *G01N 2800/04* (2013.01); *G01N 2800/042* (2013.01); *G01N 2800/32* (2013.01); *G01N 2800/324* (2013.01); *G01N 2800/325* (2013.01); *G01N 2800/347* (2013.01); *G01N 2800/52* (2013.01); *G01N 2800/56* (2013.01)

(58) Field of Classification Search
None
See application file for complete search history.

(56) References Cited

U.S. PATENT DOCUMENTS

| | | |
|---|---|---|
| 2007/0009518 A1 | 1/2007 | Novobrantseva et al. |
| 2010/0297021 A1 | 11/2010 | Wendt |
| 2015/0293119 A1 | 10/2015 | Sangaralingham |

FOREIGN PATENT DOCUMENTS

| | | |
|---|---|---|
| CN | 101247829 | 8/2008 |
| WO | WO2006125140 | 11/2006 |
| WO | WO2009016385 A1 | 2/2009 |
| WO | WO2011024973 A1 | 3/2011 |

OTHER PUBLICATIONS

Sangaralingham et al. 2011. BMC Pharmacology 2011. 11(Suppl 1):60-).*
Sangaralingham et al. 2011. BMC Pharmacology 2011. 11(Suppl 1):60.*
Flather et al., "Long-term ACE-inhibitor therapy in patients with heart failure or left-ventricular dysfunction: a systematic overview of data from individual patients. ACE-Inhibitor Myocardial Infarction Collaborative Group," Lancet, 355 (9215) 1575-1581, May 6, 2000.
European Search Report for Application No. 16173180.7, dated Jul. 19, 2016, 9 pages.
Bergijk et al., "A histologic study of the extracellular matrix during the development of glomerulosclerosis in murine chronic graft-versus-host disease," Am J Pathol., 140(5):1147-1156, May 1992.
Butkowski et al., "Basement membrane collagen in the kidney: regional localization of novel chains related to collagen IV," Kidney Int., 35(5):1195-1202, May 1989.
Canaan-Kuhl et al., "C-type natriuretic peptide inhibits mesangial cell proliferation and matrix accumulation in vivo," Kidney Int., 53(5):1143-1151, May 1998.
Canaan-Kühl et al., "Identification of "B" receptor for natriuretic peptide in human kidney," Endocrinology., 130(1):550-552, Jan. 1992.
Cataliotti et al., "CNP production in the kidney and effects of protein intake restriction in nephrotic syndrome," Am J Physiol Renal Physiol., 283(3):F464-F472, Sep. 2002.
Chrisman and Garbers, "Reciprocal antagonism coordinates C-type natriuretic peptide and mitogen-signaling pathways in fibroblasts," J Biol Chem., 274(7):4293-4299, Feb. 12, 1999.
Coresh et al., "Prevalence of chronic kidney disease in the United States," JAMA., 298(17):2038-2047, Nov. 7, 2007.
Costello-Boerrigter et al., "Amino-terminal pro-B-type natriuretic peptide and B-type natriuretic peptide in the general community. determinants and detection of left ventricular dysfunction," J Am Coll Cardiol., 47(2):345-353, Epub Jan. 4, 2006.

(Continued)

*Primary Examiner* — Shulamith H Shafer
(74) *Attorney, Agent, or Firm* — Fish & Richardson P.C.

(57) ABSTRACT

This document provides methods and materials involved in assessing renal structural alterations (e.g., renal fibrosis, glomerular basement thickening, mesangial matrix expansion, swollen podocytes, and foot processes effacement) as well as methods and materials involved in assessing outcomes. For example, methods and materials for using the level of urinary CNP (e.g., a urinary to plasma CNP ratio) to determine whether or not a mammal is developing renal structural alterations (e.g., renal fibrosis, glomerular basement thickening, mesangial matrix expansion, swollen podocytes, and foot processes effacement) as well as methods and materials for using the level of urinary CNP levels to identify patients having an increased likelihood of experiencing a poor outcome are provided.

6 Claims, 24 Drawing Sheets

(56) References Cited

OTHER PUBLICATIONS

Davidson and Sackner, "Simplification of the Anthrone Method for the Determination of Inulin in Clearance Studies," *J Lab Clin Med.*, 62:351-356, Aug. 1963.
Dean et al., "Synthesis and localization of C-type natriuretic peptide in mammalian kidney," *Am J Physiol.*, 266(3 Pt 2):F491-F496, Mar. 1994.
Del Ry et al., "C-type natriuretic peptide plasma levels increase in patients with chronic heart failure as a function of clinical severity," *Eur J Heart Fail.*, 7(7):1145-1148, Dec. 2005.
D'Souza et al., "Autocrine and paracrine actions of natriuretic peptides in the heart," *Pharmacol Ther.*, 101(2):113-129, Feb. 2004.
Floege et al., "Age-related glomerulosclerosis and interstitial fibrosis in Milan normotensive rats: a podocyte disease," *Kidney Int.*, 51(1):230-243, Jan. 1997.
Fomin and Girina, [Statins and chronic renal disease: Growth points for indications expansion]"Statiny i khronicheskaya bolezn pochek: <<tochki rosta>> dlya rasshireniya pokazaniy," *Consilium Medicum*, 12(5):105-109, 2010 [English translation].
Fox et al., "Prediction of risk of death and myocardial infarction in the six months after presentation with acute coronary syndrome: prospective multinational observational study (GRACE)," *BMJ* 333(7578):1091, Epub Oct. 10, 2006.
Furuya et al., "C-type natriuretic peptide inhibits intimal thickening after vascular injury," *Ann N Y Acad Sci..*, 748:517-523, Jan. 17, 1995.
Gandhi et al., "Causes and consequences of zinc dyshomeostasis in rats with chronic aldosteronism," *J Cardiovasc Pharmacol.*, 52(3):245-252, Sep. 2008.
Gulberg et al., "Increased renal production of C-type natriuretic peptide (CNP) in patients with cirrhosis and functional renal failure," *Gut.*, 47(6):852-857, Dec. 2000.
Harrell et al., "Multivariable prognostic models: issues in developing models, evaluating assumptions and adequacy, and measuring and reducing errors," *Stat Med.*, 15(4):361-387, Feb. 28, 1996.
Hoenig et al., "The cardiac microvasculature in hypertension, cardiac hypertrophy and diastolic heart failure," *Curr Vasc Pharmacol.*, 6(4):292-300, Oct. 2008.
Horio et al., "Gene expression, secretion, and autocrine action of C-type natriuretic peptide in cultured adult rat cardiac fibroblasts," *Endocrinology.*, 144(6):2279-2284, Jun. 2003.
Kalra et al., "C-type natriuretic peptide production by the human kidney is blunted in chronic heart failure," Clin Sci (Lond)., 118(1):71-77, Oct. 2, 2009.
Koller et al., "Selective activation of the B natriuretic peptide receptor by C-type natriuretic peptide (CNP)," *Science.*, 252(5002):120-123, Apr. 5, 1991.
Lai et al., "Gene expression and synthesis of natriuretic peptides by cultured human glomerular cells," *J Hypertens.*, 17(4):575-583, Apr. 1999.
Lewko et al., "C-type natriuretic peptide as a podocyte hormone and modulation of its cGMP production by glucose and mechanical stress," *Kidney Int.*, 66(3):1001-1008, Sep. 2004.
Mattingly et al., "Presence of C-type natriuretic peptide in human kidney and urine," *Kidney Int.*, 46(3):744-747, Sep. 1994.
McKee et al., "The natural history of congestive heart failure: the Framingham study," *N Engl J Med.*, 285(26):1441-1446, Dec. 23, 1971.
Ng et al., "Diagnosis of heart failure using urinary natriuretic peptides" *Clin Sci (Lond).*, 106(2):129-133, Feb. 2004.
Nir et al., "CNP is present in canine renal tubular cells and secreted by cultured opossum kidney cells," *Am J Physiol.*, 267(6 Pt 2):R1653-R1657, Dec. 1994.
Olivetti et al., "Cardiomyopathy of the aging human heart. Myocyte loss and reactive cellular hypertrophy," *Circ Res.*, 68(6):1560-1568, Jun. 1991.
Osawa et al., "C-Type natriuretic peptide inhibits proliferation and monocyte chemoattractant protein-1 secretion in cultured human mesangial cells," *Nephron.*, 86(4):467-472, Dec. 2000.

Parkhomenko, [Statin treatment for high-risk patients: From expectations to clinical practice] "Primenenie statinov u bolnykh vysokogo riska: put ot ozhidaniya k klinicheskoy praktike. "[Ukranian Medical Journal] Ukr.Med.Chasopis, IX/X vol. 5, No. 79, pp. 67-71, 2010. [English translation].
Pencina et al., "Evaluating the added predictive ability of a new marker: from area under the ROC curve to reclassification and beyond," *Stat Med.*, 27(2):157-172; discussion 207-12, Jan. 30, 2008.
Peralta et al., "Cystatin C identifies chronic kidney disease patients at higher risk for complications," *J Am Soc Nephrol.*, 22(1):147-155, Epub Dec. 16, 2010.
Prasad et al., "Zinc deficiency in elderly patients," *Nutrition*, 9(3):218-224, May-Jun. 1993.
Rifkin et al., "Albuminuria, impaired kidney function and cardiovascular outcomes or mortality in the elderly," *Nephrol Dial Transplant.*, 25(5):1560-1567, Epub Dec. 15, 2009.
Rule et al., "The association between age and nephrosclerosis on renal biopsy among healthy adults," *Ann Intern Med.*, 152(9):561-567, May 4, 2010.
Ruth, "Metamorphosis of the pubic symphysis: I. The white rat (*Mus norvegicus albinus*)," The Anatomical Record 64: 1-7, 1935.
Sangaralingham et al., "The aging heart, myocardial fibrosis, and its relationship to circulating C-type natriuretic Peptide," *Hypertension*, 57(2):201-207, Epub Dec. 28, 2010.
Sangaralingham et al., "Urinary C-type natriuretic peptide excretion: a potential novel biomarker for renal fibrosis during aging," *Am J Physiol Renal Physiol.*, 301(5):F943-F952, Epub Aug. 24, 2011.
Soeki et al., "C-type natriuretic peptide, a novel antifibrotic and antihypertrophic agent, prevents cardiac remodeling after myocardial infarction," *J Am Coll Cardiol.*, 45(4):608-616, Feb. 15, 2005.
Stingo et al., "Presence of C-type natriuretic peptide in cultured human endothelial cells and plasma," *Am J Physiol.*, 263(4 Pt 2):H1318-H1321, Oct. 1992.
Suga et al., "Characterization of natriuretic peptide receptors in cultured cells," *Hypertension*, 19(6 Pt 2):762-765, Jun. 1992.
Tao et al., "Biological effects of C-type natriuretic peptide in human myofibroblastic hepatic stellate cells," *J Biol Chem.*, 274(34):23761-23769, Aug. 20, 1999.
The GISEN Group (Gruppo Italiano di Studi Epidemiologici in Nefrologia), "Randomised placebo-controlled trial of effect of ramipril on decline in glomerular filtration rate and risk of terminal renal failure in proteinuric, non-diabetic nephropathy," *Lancet.*, 349(9069):1857-1863, Jun. 28, 1997.
Totsune et al., "Elevated plasma. C-type natriuretic peptide concentrations in patients with chronic renal failure," *Clin Sci (Lond).*, 87(3):319-322, Sep. 1994.
Ueno et al., "Local expression of C-type natriuretic peptide markedly suppresses neointimal formation in rat injured arteries through an autocrine/paracrine loop," *Circulation*, 96(7):2272-2279, Oct. 7, 1997.
Weber et al., "Myocardial fibrosis: functional significance and regulatory factors," *Cardiovasc Res.*, 27(3):341-348, Mar. 1993.
Weinstein and Anderson, "The aging kidney: physiological changes," *Adv Chronic Kidney Dis.*, 17(4):302-307, Jul. 2010.
Yang and Fogo, "Cell senescence in the aging kidney," *J Am Soc Nephrol.*, 21(9):1436-1439, Epub Aug. 12, 2010.
Zhou et al., "The aging kidney," *Kidney Int.*, 74(6):710-720, Epub Jul. 9, 2008.
International Search Report and Written Opinion for PCT/US2012/059670, dated Jan. 31, 2013, 8 pages.
International Preliminary Report on Patentability for PCT/US2012/059670, dated Jul. 3, 2014, 6 pages.
Supplementary Partial European Search Report for Application No. 12860343, dated Jul. 14, 2015, 7 pages.
Office Action in Chinese Application No. 201280070265.8, dated Nov. 24, 2015, 10 pages (includes English translation), 10 pages.
European Search Report for Application No. 12860343.8, dated Nov. 11, 2015, 10 pages.

* cited by examiner 2 months    11 months    20 months 2 months 11 months 20 months

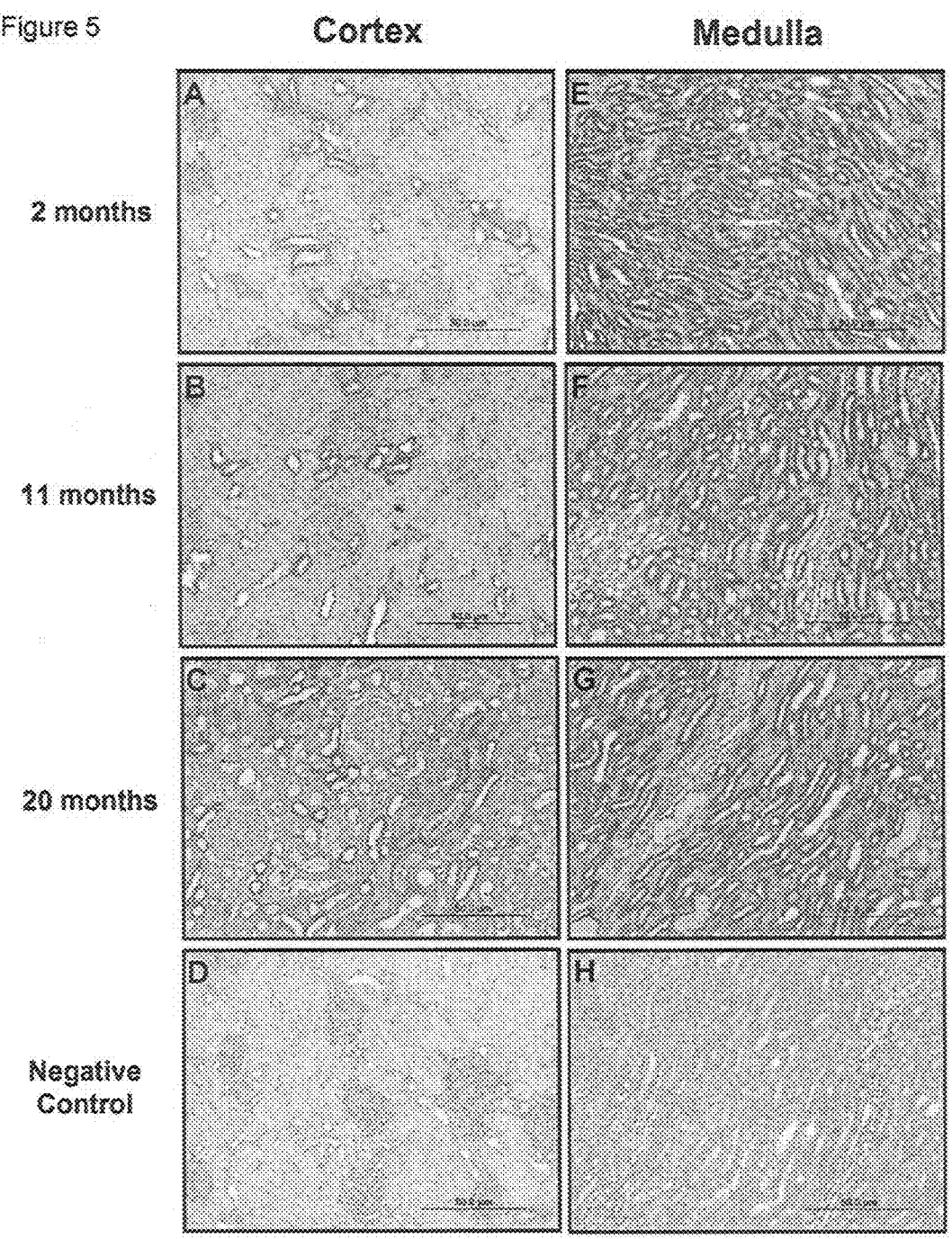

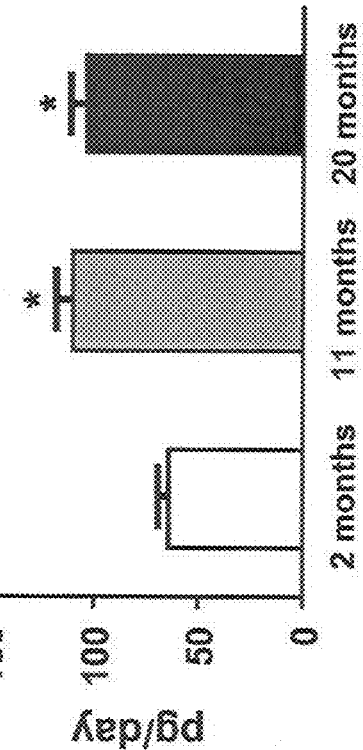
Figure 6A Plasma CNP
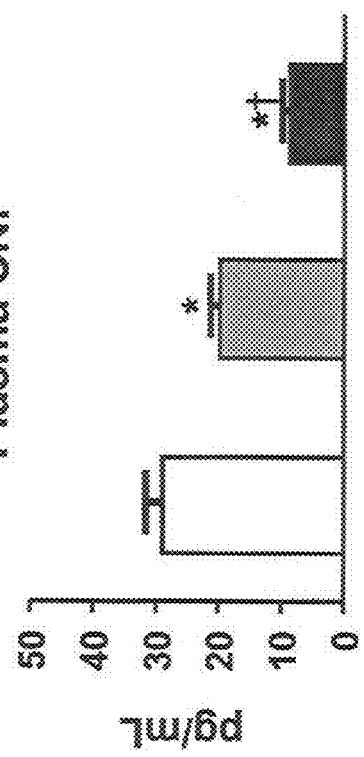
Figure 6C Urinary/Plasma CNP Ratio
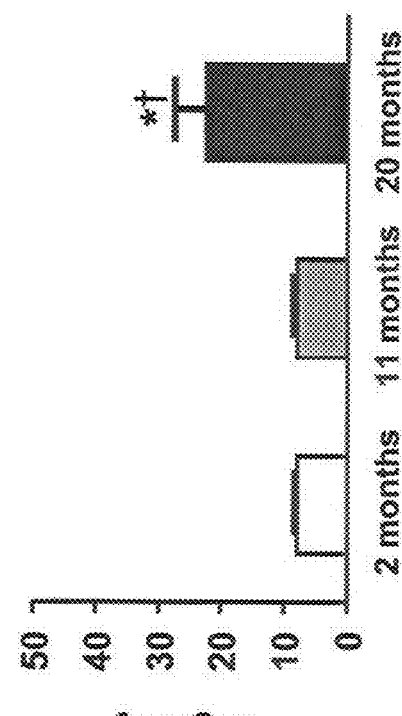
Figure 6B Urinary CNP
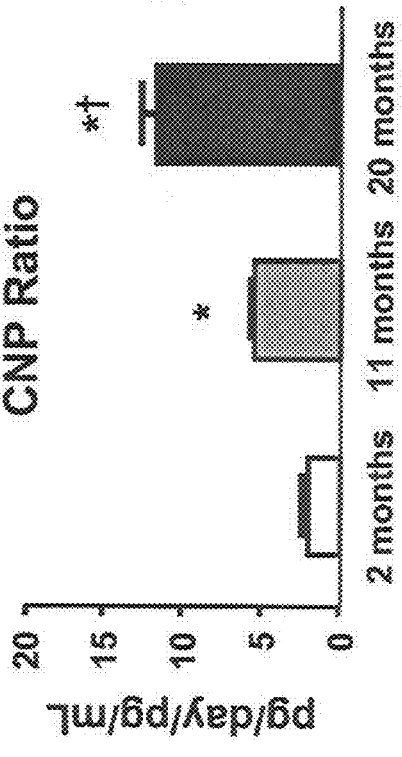
Figure 6D Proteinuria Table 1A: Human proCNP$_{1-103}$ (Molecular Form 1)

| Amino Acid # | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 |
|---|---|---|---|---|---|---|---|---|---|---|---|---|---|---|---|---|---|---|---|---|---|---|---|---|---|
| | K | P | G | A | P | P | K | V | P | R | T | P | P | A | E | E | L | A | E | P | Q | A | A | G | G |

| Amino Acid # | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 |
|---|---|---|---|---|---|---|---|---|---|---|---|---|---|---|---|---|---|---|---|---|---|---|---|---|---|
| | G | Q | K | K | G | D | K | A | P | G | G | G | G | A | N | L | K | G | D | R | S | R | L | L | R |

| Amino Acid # | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 |
|---|---|---|---|---|---|---|---|---|---|---|---|---|---|---|---|---|---|---|---|---|---|---|---|---|---|
| | D | L | R | V | D | T | K | S | R | A | A | W | A | R | L | L | Q | E | H | P | N | A | R | K | Y |

| Amino Acid # | 76 | 77 | 78 | 79 | 80 | 81 | 82 | 83 | 84 | 85 | 86 | 87 | 88 | 89 | 90 | 91 | 92 | 93 | 94 | 95 | 96 | 97 | 98 | 99 | 100 |
|---|---|---|---|---|---|---|---|---|---|---|---|---|---|---|---|---|---|---|---|---|---|---|---|---|---|
| | K | G | A | N | K | K | G | L | S | K | G | C | F | G | L | K | L | D | R | I | G | S | M | S | G |

| Amino Acid # | 101 | 102 | 103 | | | |
|---|---|---|---|---|---|---|
| | L | G | C | | SEQ ID NO:1 | |

Figure 9

Table 1B: Human NT-proCNP$_{1-50}$ (Molecular Form 2)

| Amino Acid # | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 |
|---|---|---|---|---|---|---|---|---|---|---|---|---|---|---|---|---|---|---|---|---|---|---|---|---|---|
| | K | P | G | A | P | P | K | V | P | R | T | P | P | A | E | E | L | A | E | P | Q | A | A | G | G |

| Amino Acid # | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 |
|---|---|---|---|---|---|---|---|---|---|---|---|---|---|---|---|---|---|---|---|---|---|---|---|---|---|
| | G | Q | K | G | D | K | A | P | G | G | G | G | A | N | L | K | G | D | R | S | R | L | L | L | R |

SEQ ID NO:2

Table 1C: Human CNP-53$_{51-103}$ (Molecular Form 3)

| Amino Acid # | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 |
|---|---|---|---|---|---|---|---|---|---|---|---|---|---|---|---|---|---|---|---|---|---|---|---|---|---|
| | D | L | R | V | D | T | K | S | R | A | A | W | A | R | L | L | Q | E | H | P | N | A | R | K | Y |

| Amino Acid # | 76 | 77 | 78 | 79 | 80 | 81 | 82 | 83 | 84 | 85 | 86 | 87 | 88 | 89 | 90 | 91 | 92 | 93 | 94 | 95 | 96 | 97 | 98 | 99 | 100 |
|---|---|---|---|---|---|---|---|---|---|---|---|---|---|---|---|---|---|---|---|---|---|---|---|---|---|
| | K | G | A | N | K | K | G | L | S | K | G | C | F | G | L | K | L | D | R | I | G | S | M | S | G |

| Amino Acid # | 101 | 102 | 103 |
|---|---|---|---|
| | L | G | C |

SEQ ID NO:3

Figure 9 (continued)

Table 1D: Human NT-CNP-53₅₁₋₈₁ (Molecular Form 4)

| Amino Acid # | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 |
|---|---|---|---|---|---|---|---|---|---|---|---|---|---|---|---|---|---|---|---|---|---|---|---|---|---|
| | D | L | R | V | D | T | K | S | R | A | A | W | A | R | L | L | Q | E | H | P | N | A | R | K | Y |

| Amino Acid # | 76 | 77 | 78 | 79 | 80 | 81 |
|---|---|---|---|---|---|---|
| | K | G | A | N | K | K |

SEQ ID NO:4

Table 1E: Human CNP-22₈₂₋₁₀₃ (Molecular Form 5)

| Amino Acid # | 82 | 83 | 84 | 85 | 86 | 87 | 88 | 89 | 90 | 91 | 92 | 93 | 94 | 95 | 96 | 97 | 98 | 99 | 100 | 101 | 102 | 103 |
|---|---|---|---|---|---|---|---|---|---|---|---|---|---|---|---|---|---|---|---|---|---|---|
| | G | L | S | K | G | C | F | G | L | K | L | D | R | I | G | S | M | S | G | L | G | C |

SEQ ID NO:5

Figure 9 (continued)

Table 1F: Human NT-proCNP$_{1-81}$ (Molecular Form 6)

| Amino Acid # | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 |
|---|---|---|---|---|---|---|---|---|---|---|---|---|---|---|---|---|---|---|---|---|---|---|---|---|---|
| | K | P | G | A | P | P | K | V | P | R | T | P | P | A | E | E | L | A | E | P | Q | A | A | G | G |

| Amino Acid # | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 |
|---|---|---|---|---|---|---|---|---|---|---|---|---|---|---|---|---|---|---|---|---|---|---|---|---|---|
| | G | Q | K | K | G | D | K | A | P | G | G | G | G | A | N | L | K | G | D | R | S | R | L | L | R |

| Amino Acid # | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 |
|---|---|---|---|---|---|---|---|---|---|---|---|---|---|---|---|---|---|---|---|---|---|---|---|---|---|
| | D | L | R | V | D | T | K | S | R | A | A | W | A | R | L | L | Q | E | H | P | N | A | R | K | Y |

| Amino Acid # | 76 | 77 | 78 | 79 | 80 | 81 |
|---|---|---|---|---|---|---|
| | K | G | A | N | K | K |

SEQ ID NO: 6

Figure 9 (continued)

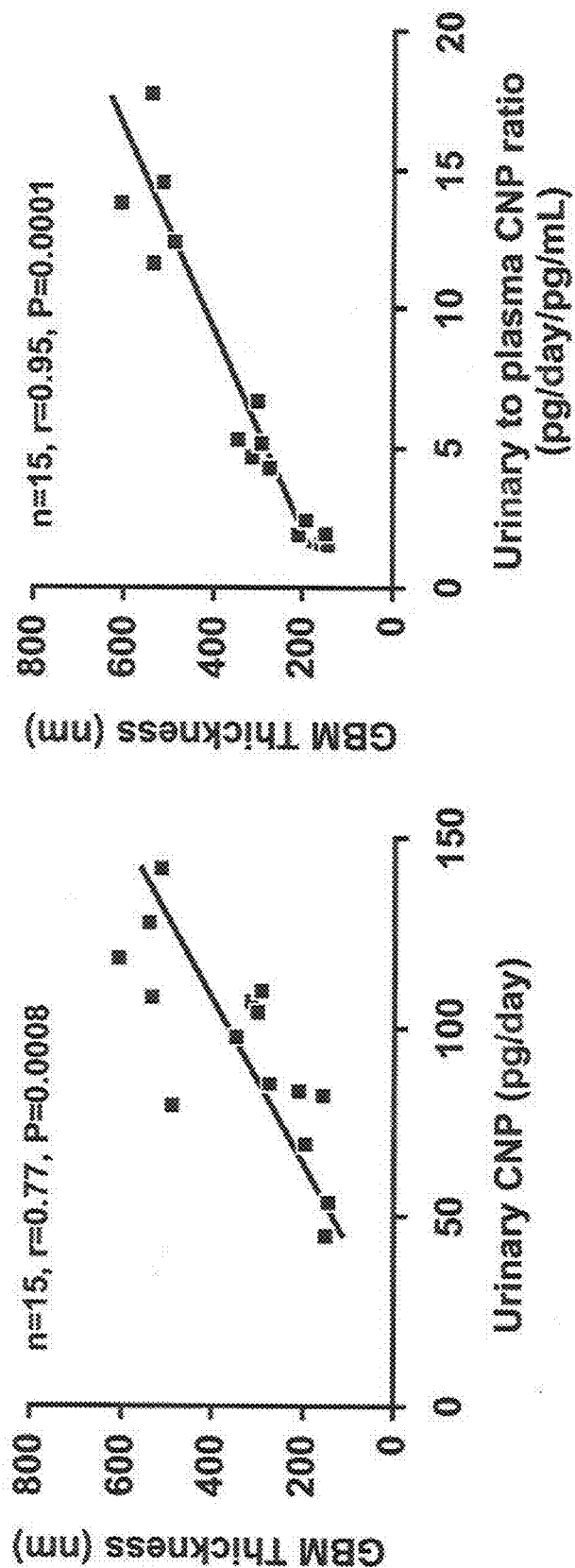

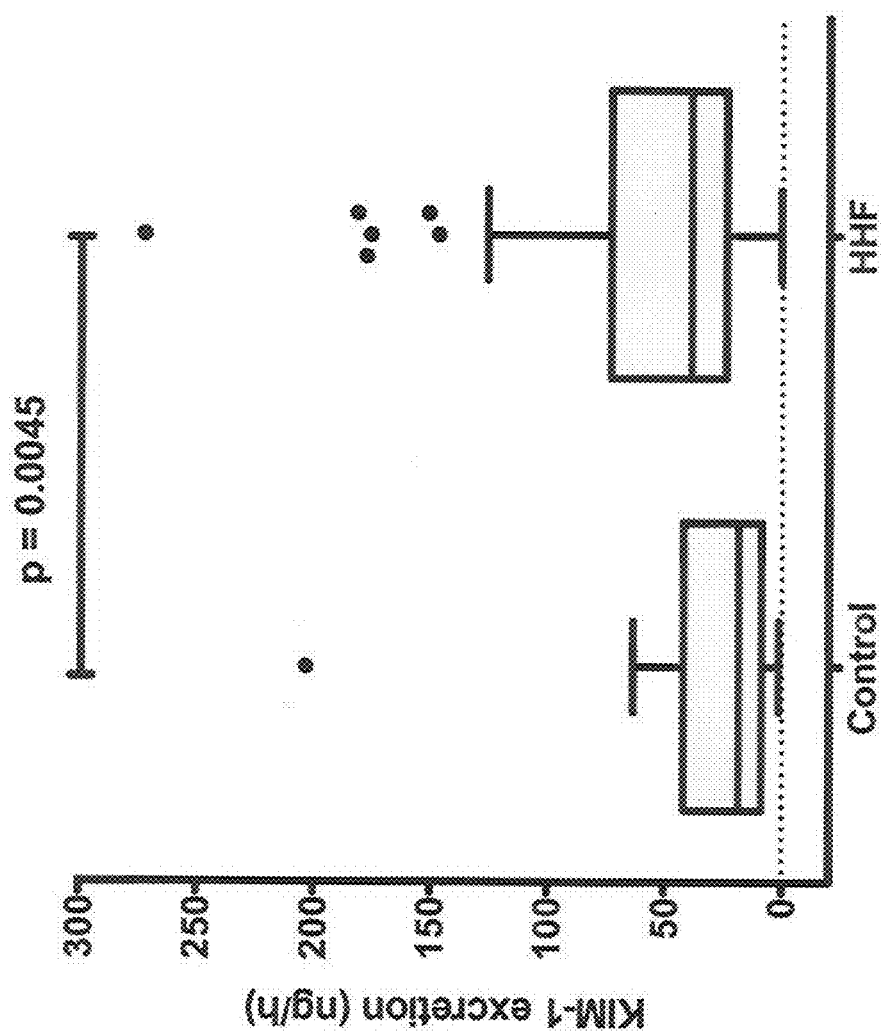

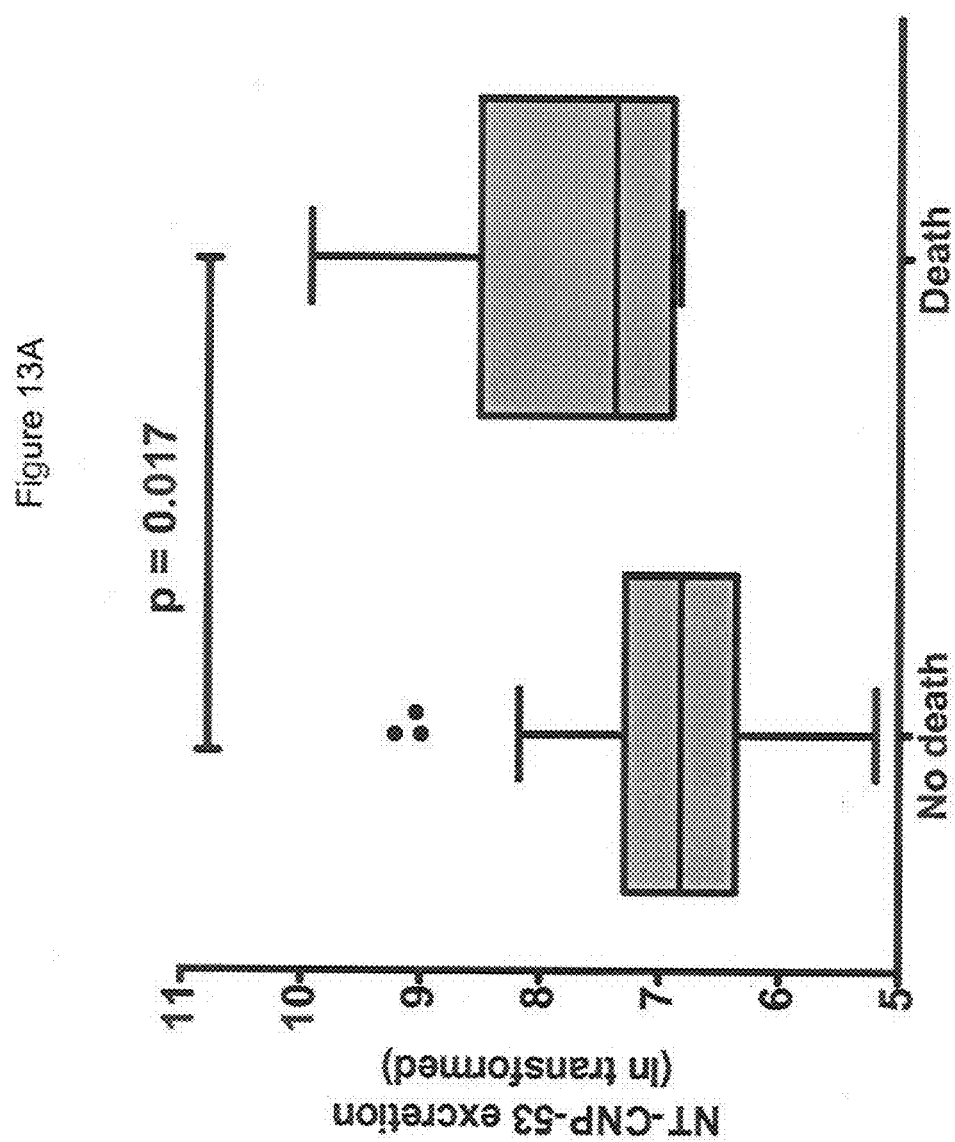

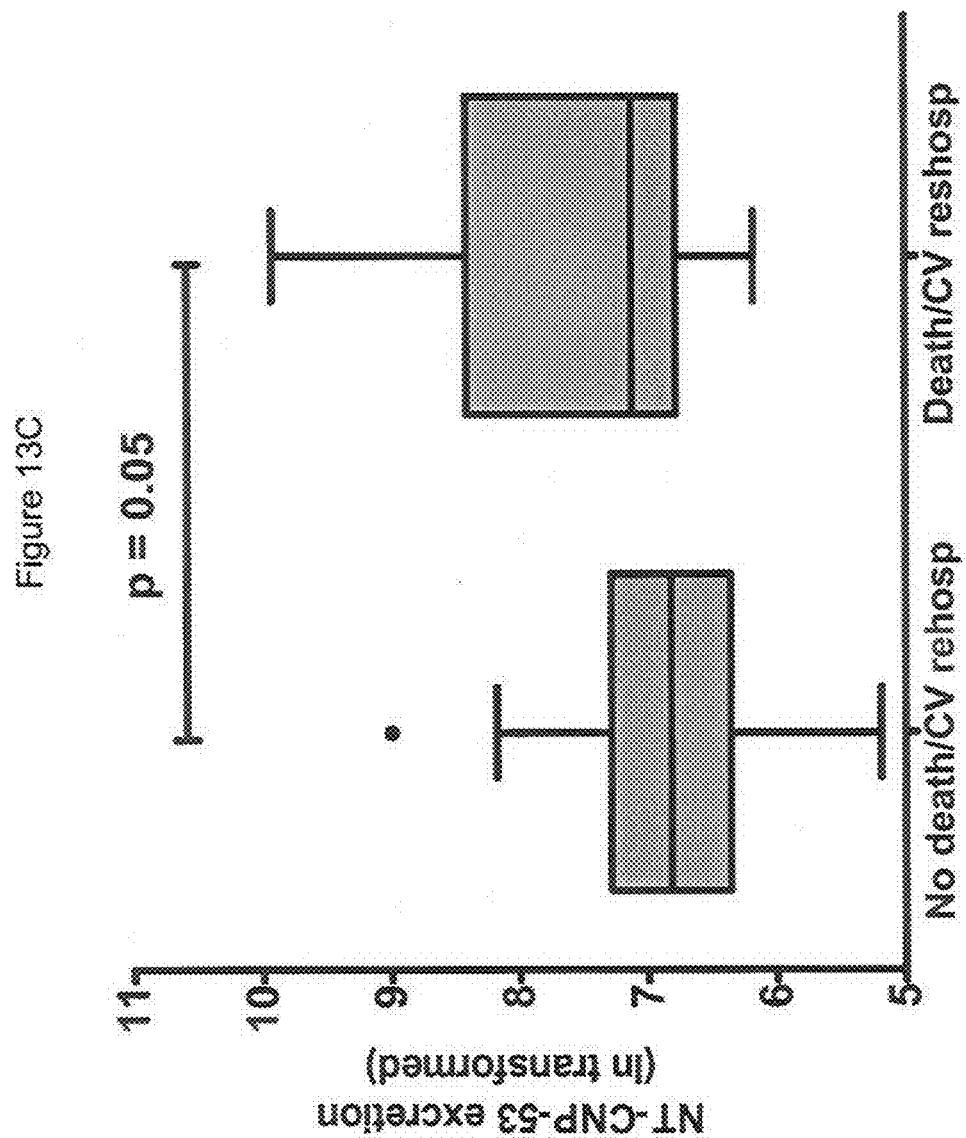

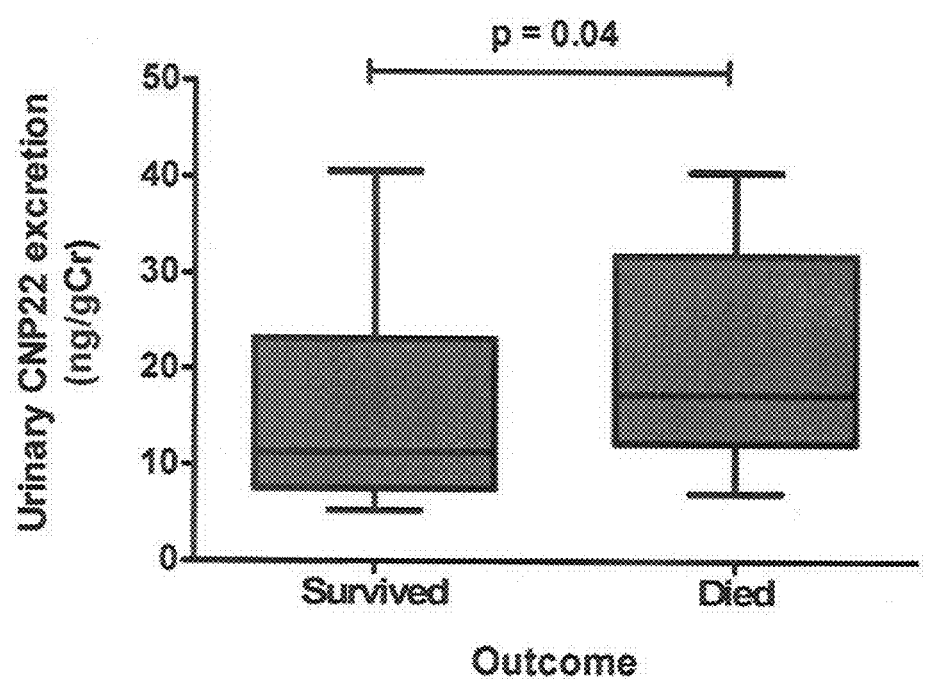

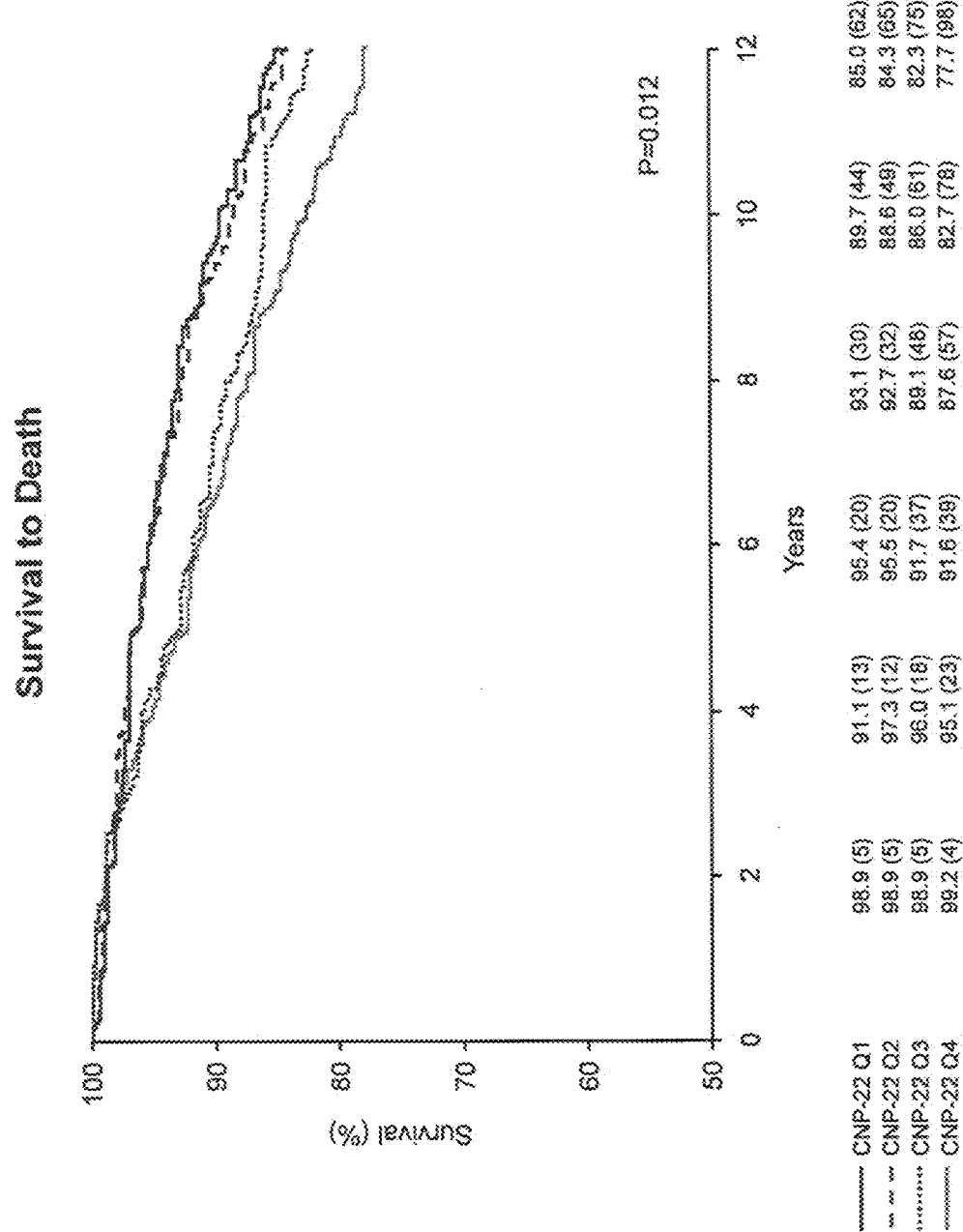

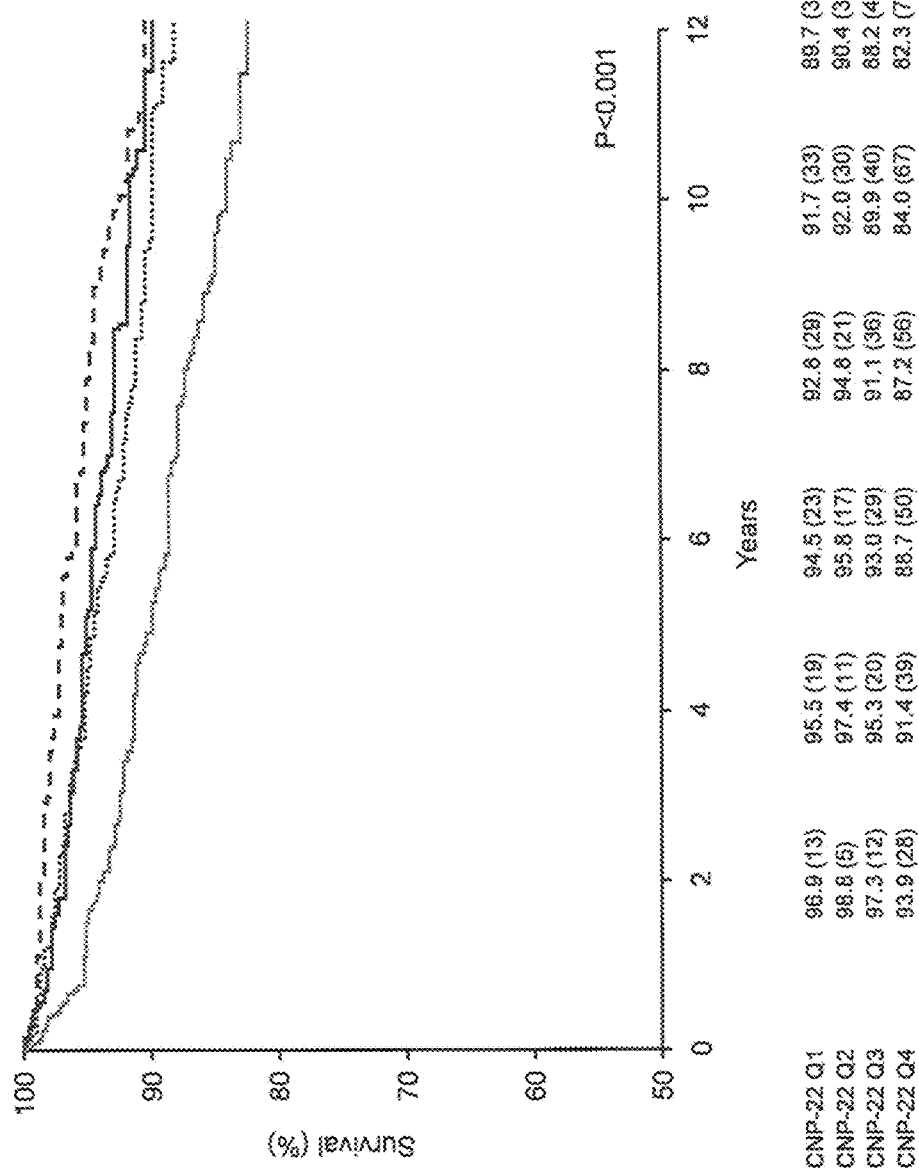

ASSESSING RENAL STRUCTURAL ALTERATIONS AND OUTCOMES

CROSS-REFERENCE TO RELATED APPLICATIONS

This application is a continuation of U.S. application Ser. No. 14/367,185, filed Jun. 19, 2014, which is a National Stage application under 35 U.S.C. §371 of International Application No. PCT/US2012/059670, filed Oct. 11, 2012, which claims the benefit of U.S. Provisional Application Ser. No. 61/580,139, filed Dec. 23, 2011. The disclosure of the prior applications are considered part of (and are incorporated by reference in) the disclosure of this application.

STATEMENT AS TO FEDERALLY SPONSORED RESEARCH

This invention was made with government support under grants HL036634 and HL076611 awarded by National Institutes of Health. The government has certain rights in the invention.

BACKGROUND

1. Technical Field

This document relates to methods and materials involved in assessing renal structural alterations (e.g., renal fibrosis) as well as methods and materials involved in assessing outcomes. For example, this document relates to methods and materials for using the level of urinary C-type natriuretic peptide (CNP) (e.g., a urinary to plasma CNP ratio) or the level of plasma CNP to determine whether or not a mammal is developing renal structural alterations (e.g., renal fibrosis, glomerular basement thickening, swollen podocytes, and foot processes effacement). This document also relates to methods and materials for using the level of urinary or plasma CNP, which can include six molecular CNP forms, levels to identify heart failure patients having an increased likelihood of experiencing a poor outcome and who may have disease processes known to involve the kidney including, but not limited to, heart failure, hypertension, diabetes, metabolic syndrome, and chronic kidney disease 2. Background Information C-type natriuretic peptide (CNP) is part of the natriuretic peptide family, produced in the kidney as well as the endothelium and can be detected in the plasma and urine. It is synthesized as the precursor 103 amino acid (AA) protein, proCNP (AA 1-103), which is then cleaved into CNP-53 (AA 51-103) and NT-proCNP (AA 1-50) by the intracellular endoprotease furin. Additional downstream processing, by an unknown enzyme, cleaves CNP-53 to give rise to the primary biologically active form CNP-22 (AA 82-103) and its amino-terminal, NT-CNP-53 (51-81).

CNP possesses potent anti-fibrotic and anti-proliferative properties through the activation of the natriuretic peptide receptor B (NPR-B), otherwise known as guanylyl cyclase receptor B (GC-B), and the generation of the second messenger 3',5'-cyclic guanosine monophosphate (cGMP). CNP has limited natriuretic and diuretic actions.

SUMMARY

This document provides methods and materials involved in assessing renal structural alterations (e.g., renal fibrosis, glomerular basement thickening, swollen podocytes, and foot processes effacement). For example, this document provides methods and materials for using the level of urinary CNP (e.g., a urinary to plasma CNP ratio) and/or the level of plasma CNP to determine whether or not a mammal is developing or is likely to develop renal structural alterations (e.g., renal fibrosis, glomerular basement thickening, mesangial matrix expansion, swollen podocytes, and foot processes effacement). Determining if a human patient is developing or is likely to develop renal structural alterations by assessing the level of urinary or plasma CNP (e.g., a urinary to plasma CNP ratio) can aid in the identification of humans with preclinical renal structural changes prior to the onset of symptoms and disease, thereby allowing for the initiation of strategies designed to prevent the progression of chronic kidney disease.

This document also provides methods and materials involved in assessing heart failure outcomes. For example, this document provides methods and materials for using the level of urinary or plasma CNP and/or its six possible molecular forms (FIG. 8) to identify humans having an increased likelihood of experiencing a poor outcome. Identify patients as having an increased likelihood of experiencing a poor outcome based at least in part on an elevated level of urinary CNP and/or a reduced level of plasma CNP can aid physicians and patients in making proper treatment decisions.

In general, one aspect of this document features a method for assessing renal structure. The method comprises, or consist essentially of, determining whether or not a mammal contains an elevated urinary CNP to plasma CNP ratio, wherein the presence of the elevated urinary CNP to plasma CNP ratio indicates that the mammal contains or is likely to experience renal structural alterations, and wherein the absence of the elevated urinary CNP to plasma CNP ratio indicates that the mammal does not contain and is not likely to experience the renal structural alterations. The mammal can be a human. The renal structural alterations can include renal fibrosis. The elevated urinary CNP to plasma CNP ratio can be greater than 12,000 pg/day to 16 pg/mL. The elevated urinary CNP to plasma CNP ratio can be greater than 13,200 pg/day to 18 pg/mL.

In another aspect, this document features a method for assessing renal structure. The method comprises, or consists essentially of, determining whether or not a mammal contains an elevated urinary CNP-22 to plasma CNP-22 ratio, wherein the presence of the elevated urinary CNP-22 to plasma CNP-22 ratio indicates that the mammal contains or is likely to experience renal structural alterations, and wherein the absence of the elevated urinary CNP-22 to plasma CNP-22 ratio indicates that the mammal does not contain and is not likely to experience the renal structural alterations. The mammal can be a human. The renal structural alterations can include renal fibrosis. The elevated urinary CNP-22 to plasma CNP-22 ratio can be greater than 12,000 pg/day to 16 pg/mL. The elevated urinary CNP-22 to plasma CNP-22 ratio can be greater than 13,200 pg/day to 18 pg/mL.

In another aspect, this document features a method for assessing renal structure. The method comprises, or consists essentially of, (a) detecting the presence of an elevated urinary CNP to plasma CNP ratio in a mammal, and (b) classifying the mammal as having or as likely to experience a renal structural alteration based at least in part on the presence. The mammal can be a human. The renal structural alteration can include renal fibrosis. The elevated urinary CNP to plasma CNP ratio can be greater than 12,000 pg/day to 16 pg/mL. The elevated urinary CNP to plasma CNP ratio can be greater than 13,200 pg/day to 18 pg/mL.

In another aspect, this document features a method for assessing renal structure. The method comprises, or consists essentially of, (a) detecting the presence of an elevated urinary CNP-22 to plasma CNP-22 ratio in a mammal, and (b) classifying the mammal as having or as likely to experience a renal structural alteration based at least in part on the presence. The mammal can be a human. The renal structural alteration can include renal fibrosis. The elevated urinary CNP-22 to plasma CNP-22 ratio can be greater than 12,000 pg/day to 16 pg/mL. The elevated urinary CNP-22 to plasma CNP-22 ratio can be greater than 13,200 pg/day to 18 pg/mL.

In another aspect, this document features a method for assessing outcomes. The method comprises, or consists essentially of, determining whether or not a mammal having experienced a disease process contains an elevated level of urinary CNP, wherein the presence of the elevated level indicates that the mammal is likely to experience a poor outcome, and wherein the absence of the level indicates that the mammal is not likely to experience the poor outcome. The mammal can be a human. The disease process can be heart failure, hypertension, diabetes, metabolic syndrome, or chronic kidney disease. The poor outcome can be death, hospitalization, heart failure, myocardial infarction, worsening renal function, worsening cardiac function, or dialysis. The urinary CNP can be urinary NT-CNP-53. The elevated level can be greater than 36,000 pg of NT-CNP-53/day. The elevated level can be greater than 42,000 pg of NT-CNP-53/day.

In another aspect, this document features a method for assessing outcomes. The method comprises, or consists essentially of, (a) detecting the presence of an elevated urinary CNP in a mammal having experienced a disease process, and (b) classifying the mammal as likely to experience a poor outcome based at least in part on the presence. The mammal can be a human. The disease process can be heart failure, hypertension, diabetes, metabolic syndrome, or chronic kidney disease. The poor outcome can be death, hospitalization, heart failure, myocardial infarction, worsening renal function, worsening cardiac function, or dialysis. The urinary CNP can be urinary NT-CNP-53. The elevated level can be greater than 36,000 pg of NT-CNP-53/day. The elevated level can be greater than 42,000 pg of NT-CNP-53/day.

In another aspect, this document features a method for assessing renal structure. The method comprises, or consists essentially of, (a) performing an immunoassay with an anti-CNP antibody to detect an elevated urinary CNP to plasma CNP ratio of a mammal, and (b) classifying the mammal as containing or as likely to experience renal structural alterations. The mammal can be a human. The renal structural alterations can comprise renal fibrosis. The elevated urinary CNP to plasma CNP ratio can be greater than 12,000 pg/day to 16 pg/mL. The elevated urinary CNP to plasma CNP ratio can be greater than 13,200 pg/day to 18 pg/mL.

In another aspect, this document features a method for assessing renal structure. The method comprises, or consists essentially of, (a) performing an immunoassay with an anti-CNP antibody to detect an elevated urinary CNP-22 to plasma CNP-22 ratio of a mammal, and (b) classifying the mammal as containing or as likely to experience renal structural alterations. The mammal can be a human. The renal structural alterations can comprise renal fibrosis. The elevated urinary CNP-22 to plasma CNP-22 ratio can be greater than 12,000 pg/day to 16 pg/mL. The elevated urinary CNP-22 to plasma CNP-22 ratio can be greater than 13,200 pg/day to 18 pg/mL.

In another aspect, this document features a method for assessing outcomes. The method comprises, or consists essentially of, (a) performing an immunoassay with an anti-CNP antibody to detect the presence of an elevated level of urinary CNP in a mammal having experienced a disease process, and (b) classifying the mammal as likely to experience a poor outcome based at least in part on the presence. The mammal can be a human. The disease process can be heart failure, hypertension, diabetes, metabolic syndrome, or chronic kidney disease. The poor outcome can be death, hospitalization, heart failure, myocardial infarction, worsening renal function, worsening cardiac function, or dialysis. The urinary CNP can be urinary NT-CNP53. The elevated level can be greater than 36,000 pg of NT-CNP53/day. The elevated level can be greater than 42,000 pg of NT-CNP53/day.

In another aspect, this document features a method for assessing a mammal for an increased risk of death or myocardial infarction. The method comprises, or consists essentially of, determining whether or not the mammal contains an elevated level of plasma CNP-22, wherein the presence of the elevated level indicates that the mammal is likely to experience the death or myocardial infarction sooner than a comparable mammal lacking the elevated level, and wherein the absence of the elevated level indicates that the mammal is likely to experience the death or myocardial infarction later than a comparable mammal having the elevated level. The mammal can be a human. The elevated level can be greater than 14 pg/mL. The elevated level can be greater than 16 pg/mL.

In another aspect, this document features a method for assessing a mammal for an increased risk of death or myocardial infarction. The method comprises, or consists essentially of, (a) performing an immunoassay with an anti-CNP antibody to detect the presence of an elevated level of plasma CNP-22 in a mammal, and (b) classifying the mammal as likely to experience death or myocardial infarction based at least in part on the presence. The mammal can be a human. The elevated level can be greater than 14 pg/mL. The elevated level can be greater than 16 pg/mL. The method can comprise classifying the mammal as likely to experience death or myocardial infarction sooner than a comparable mammal lacking the elevated level.

In another aspect, this document features a method for treating a mammal having an increased risk of a renal structural alteration. The method comprises, or consists essentially of, (a) determining that the mammal has an elevated urinary CNP to plasma CNP ratio, (b) monitoring the mammal for the presence of a risk factor for renal structural alteration, and (c) instructing the mammal to administer a therapeutic agent to reduce a symptom of the renal structural alteration. The mammal can be a human. The elevated urinary CNP to plasma CNP ratio can be greater than 12,000 pg/day to 16 pg/mL. The elevated urinary CNP to plasma CNP ratio can be greater than 13,200 pg/day to 18 pg/mL. The risk factor can be selected from the group consisting of an age factor, hypertension, an elevated serum creatinine level, proteinuria, an elevated body mass index, an elevated cholesterol level, a smoking habit, and diabetes. The therapeutic agent can be an ACE inhibitor, an angiotensin receptor blocker, an aldosterone antagonist, a statin, a native natriuretic peptide, or a designer natriuretic peptide.

In another aspect, this document features a method for treating a mammal having an increased risk of a poor outcome. The method comprises, or consists essentially of, (a) determining that the mammal has an elevated level of urinary CNP, (b) monitoring the mammal for the presence of a risk factor for a poor outcome, and (c) instructing the mammal to administer a therapeutic agent to reduce the likelihood of the poor outcome. The mammal can be a human. The urinary CNP can be urinary NT-CNP-53. The elevated level can be greater than 36,000 pg of NT-CNP-53/day. The elevated level can be greater than 42,000 pg of NT-CNP-53/day. The risk factor can be selected from the group consisting of an age factor, hypertension, an elevated serum creatinine level, proteinuria, an elevated body mass index, an elevated cholesterol level, a smoking habit, and diabetes. The therapeutic agent can be an ACE inhibitor, an angiotensin receptor blocker, an aldosterone antagonist, a statin, a native natriuretic peptide, or a designer natriuretic peptide.

In another aspect, this document features a method for treating a mammal having an increased risk of myocardial infarction. The method comprises, or consists essentially of, (a) determining that the mammal has an elevated level of plasma CNP-22, (b) monitoring the mammal for the presence of a risk factor for myocardial infarction, and (c) instructing the mammal to administer a therapeutic agent to reduce the risk of myocardial infarction. The mammal can be a human. The elevated level can be greater than 14 pg/mL. The elevated level can be greater than 16 pg/mL. The risk factor can be selected from the group consisting of an age factor, hypertension, an elevated serum creatinine level, proteinuria, an elevated body mass index, an elevated cholesterol level, a smoking habit, and diabetes. The therapeutic agent can be an ACE inhibitor, an angiotensin receptor blocker, an aldosterone antagonist, a statin, a native natriuretic peptide, or a designer natriuretic peptide.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 5. Representative images at 20× objective magnification of the immunohistochemical localization of renal cortical and medullary CNP from 2, 11, and 20 month old Fischer rats.

FIGS. 6A-D. Changes in plasma CNP (A), urinary CNP excretion (B), urinary to plasma CNP ratio (C), and proteinuria (D) between 2, 11, and 20 month old Fischer rats. Values are mean±SE. n=10 for all age groups. *P<0.05 vs. 2 months, †P<0.05 vs. 11 months.

FIG. 9 is a listing of the amino acid sequences of the molecular forms of CNP.

FIGS. 11A-B. Correlations between glomerular basement membrane (GBM) thickness and urinary CNP excretion (A) as well as between GBM thickness and urinary to plasma CNP (B).

FIG. 12. Urinary KIM-1 excretion in ADHF patients (HHF) vs. controls. Outlier box plots displayed with median and interquartile ranges (IQR; box) and 1.5*IQR (error bars) for 24 h KIM-1 excretion values.

FIGS. 13A-C. Association between NT-CNP-53 excretion and clinical outcomes: (A) mortality, (B) time to first non-elective (all-cause) rehospitalization/death, (C) time to first non-elective cardiovascular rehospitalization/death. Outlier box plots displayed with median and interquartile ranges (IQR; box) and 1.5*IQR (error bars) for 24 h NT-CNP-53 excretion values (natural logarithmic transformed data).

FIGS. 14A-C. Urinary excretion of CNP molecular forms by primary outcome (mortality) in ADHF. Outlier box plots displayed with median and interquartile ranges (IQR; box) and 1.5*IQR (error bars) for 24 hour urinary (A) CNP22, (B) CNP53, and (C) NT-CNP53 excretion values against mortality in ADHF.

FIGS. 15A-B. Kaplan-Meier curves for death (A) and myocardial infarction (MI; B) in the general population according to quartiles of plasma CNP-22 levels. CNP-22 Q1 is from 2.0 to 10.1 pg/mL; CNP-22 Q2 is from 10.2 to 13.1 pg/mL; CNP-22 Q3 is from 13.2 to 16.7 pg/mL; and CNP-22 Q4 is from 16.8 to 265.0 pg/mL.

DETAILED DESCRIPTION

This document provides methods and materials involved in assessing renal structural alterations (e.g., renal fibrosis). For example, this document provides methods and materials for using the level of urinary CNP (e.g., a urinary to plasma CNP ratio) and/or the level of plasma CNP to determine whether or not a mammal is developing or is likely to develop a renal structural alteration. As described herein, the presence of an elevated level of urinary CNP, a reduced level of plasma CNP, and/or an elevated level of a urinary to plasma CNP ratio can indicate that the mammal is developing or is likely to develop a renal structural alteration. Examples of renal structural alteration include, without limitation, renal fibrosis, glomerular basement membrane thickening, mesangial matrix expansion, swollen podocytes, and foot processes effacement. The methods and materials provided herein can be used to assess renal structural alterations in any appropriate mammal including, without limitation, humans, monkeys, horses, cows, sheep, goats, mice, and rats.

Figure 8:
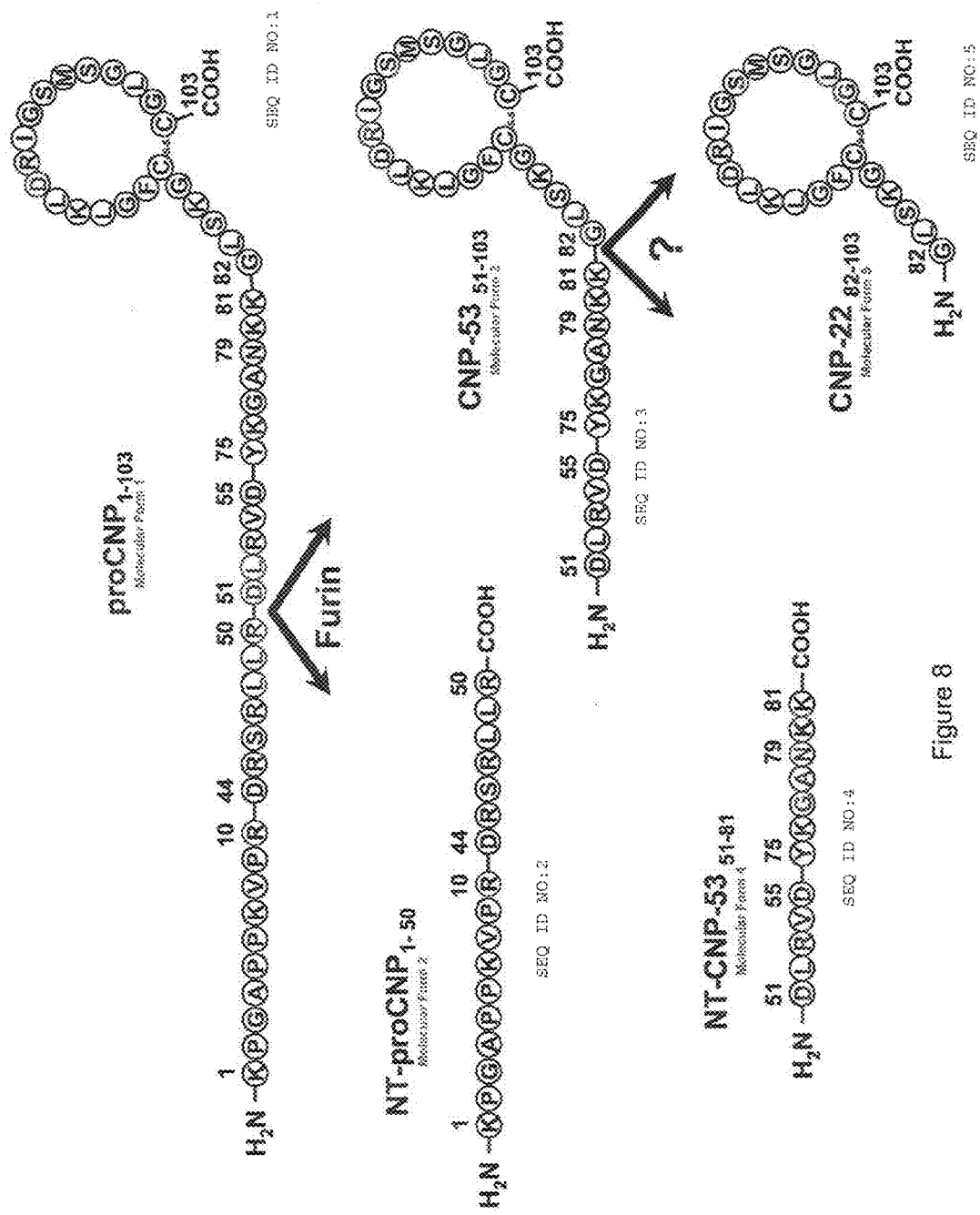
FIG. 8 is a diagram of the molecular forms of CNP.
Figure 8:
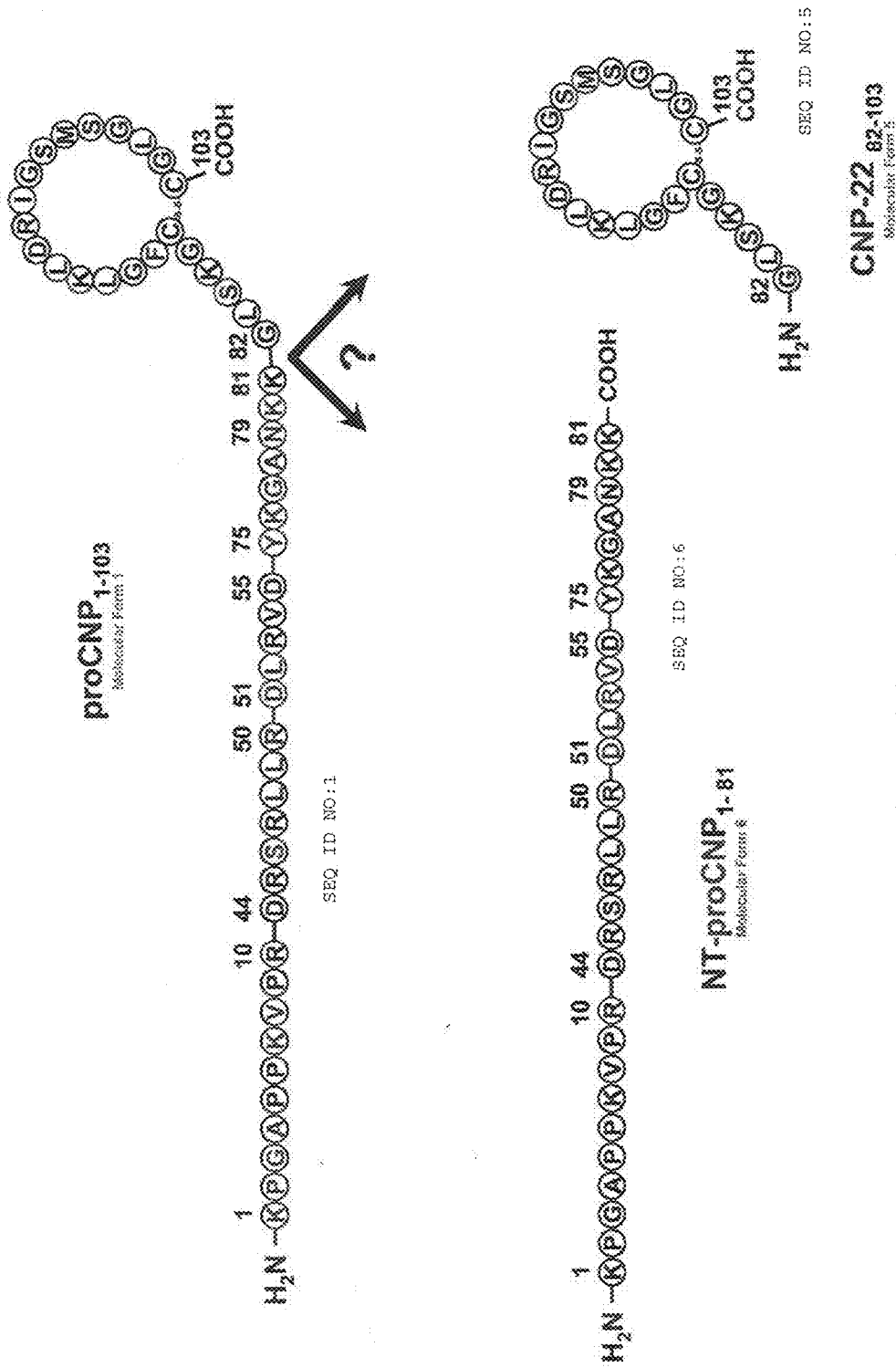

The amino acid sequences of six molecular forms of human CNP are set forth in FIGS. 8 and 9.

The term "elevated level" as used herein with respect to the plasma or urinary level of CNP (or a particular molecular form of CNP such as CNP-53) refers to any level that is above a median plasma or urinary level for an age-matched random population of healthy mammals (e.g., an age-matched random population of 10, 20, 30, 40, 50, 100, or 500 healthy mammals) that do not have renal disease. In some cases, an elevated level of plasma CNP (e.g., plasma CNP-22) can be any level that is greater than 16 pg/mL. In some cases, an elevated level of urinary CNP (e.g., urinary CNP-22) can be any level that is greater than 12,000 pg/day.

The term "elevated" as used herein with respect to a urinary CNP to plasma CNP ratio refers to any ratio level that is above an average urinary CNP to plasma CNP ratio for an age-matched random population of healthy mammals (e.g., an age-matched random population of 10, 20, 30, 40, 50, 100, or 500 healthy mammals) that do not have renal disease. In some cases, an elevated urinary CNP to plasma CNP ratio can be a ratio that is greater than 12,000 pg/day urinary CNP to 16 pg/mL plasma CNP. In some cases, a plasma CNP to urinary CNP ratio can be used in place of a urinary CNP to plasma CNP ratio.

In some cases, the presence of a reduced level of plasma CNP can indicate that the mammal is developing or is likely to develop a renal structural alteration or is likely to experience a poor outcome. The term "reduced level" as used herein with respect to the plasma level of CNP refers to any level that is below a median plasma level for an age-matched random population of healthy mammals (e.g., an age-matched random population of 10, 20, 30, 40, 50, 100, or 500 healthy mammals) that do not have renal disease. In some cases, a reduced level of plasma CNP can be any level that is less than 10 pg/mL.

In some cases, the presence of a reduced level of plasma CNP, an elevated level of urinary CNP, and an elevated level of plasma NT-proBNP can indicate that the mammal is developing or is likely to develop a renal structural alteration or is likely to experience a poor outcome. The term "elevated level" as used herein with respect to the plasma level of NT-proBNP refers to any level that is above a median plasma level for an age-matched random population of healthy mammals (e.g., an age-matched random population of 10, 20, 30, 40, 50, 100, or 500 healthy mammals) that do not have renal disease. In some cases, an elevated level of plasma NT-proBNP can be any level that is greater than 450 pg/mL.

Any appropriate method can be used to determine a urinary CNP level, a plasma CNP level, a urinary CNP to plasma CNP ratio, a plasma NT-proBNP level, or a plasma CNP to urinary CNP ratio. For example, polypeptide detection methods such as immunoassays (e.g., ELISAs or radioimmunoassays) and mass spectrometry can be used to determine the level of CNP in a plasma or urine sample. In some cases, radioimmunoassays can be used to determine the urinary CNP to plasma CNP ratio.

This document also provides methods and materials involved in assessing outcomes. For example, this document provides methods and materials for using the level of urinary CNP or its six possible molecular forms (e.g., CNP-53 or NT-CNP-53) to determine whether or not a mammal is likely to experience a poor outcome. As described herein, the presence of an elevated level of urinary CNP can indicate that the mammal is likely to experience a poor outcome. Examples of poor outcomes include, without limitation, death, hospitalization, heart failure, myocardial infarction, worsening renal function, worsening cardiac function, and dialysis. The methods and materials provided herein can be used to assess outcomes in any appropriate mammal including, without limitation, humans, monkeys, horses, cows, sheep, and goats.

In some cases, the term "elevated level" as used herein with respect to the urinary level of NT-CNP-53 can refer to any level that is above a median urinary NT-CNP-53 level for an age-matched random population of healthy mammals (e.g., an age-matched random population of 10, 20, 30, 40, 50, 100, or 500 healthy mammals) that do not have a history of other co-morbidities such as heart failure, hypertension, diabetes, metabolic syndrome, or chronic kidney disease. In some cases, an elevated level of urinary NT-CNP-53 can be any level that is greater than 36,000 pg/day.

This document also provides methods and materials to assist medical or research professionals in determining whether or not a mammal is developing or is likely to develop a renal structural alteration as well as methods and materials to assist medical or research professionals in determining whether or not a mammal is likely to experience a poor outcome. Medical professionals can be, for example, doctors, nurses, medical laboratory technologists, and pharmacists. Research professionals can be, for example, principal investigators, research technicians, postdoctoral trainees, and graduate students. A professional can be assisted in determining whether or not a mammal is developing or is likely to develop a renal structural alteration by (1) determining a urinary CNP level, a plasma CNP level, a urinary CNP to plasma CNP ratio, or a plasma CNP to urinary CNP ratio, and (2) communicating information about that level or ratio to that professional. A professional can be assisted in determining whether or not a mammal is likely to experience a poor outcome by (1) determining a urinary CNP level, and (2) communicating information about that level to that professional.

Any method can be used to communicate information to another person (e.g., a professional). For example, information can be given directly or indirectly to a professional. In addition, any type of communication can be used to communicate the information. For example, mail, e-mail, telephone, and face-to-face interactions can be used. The information also can be communicated to a professional by making that information electronically available to the professional. For example, the information can be communicated to a professional by placing the information on a computer database such that the professional can access the information. In addition, the information can be communicated to a hospital, clinic, or research facility serving as an agent for the professional.

This document also provides methods and materials for treating a mammal that is developing or is likely to develop a renal structural alteration. For example, a mammal can be assessed to determine if the mammal has an elevated urinary CNP to plasma CNP ratio. As described herein, mammals having an elevated urinary CNP to plasma CNP ratio can be developing or can be likely to develop a renal structural alteration. Once a mammal is identified as having an elevated urinary CNP to plasma CNP ratio, that mammal can be monitored for the presence of one or more risk factors for a renal structural alteration. For example, the mammal can be monitored or evaluated for the presence of an age factor, hypertension, an elevated serum creatinine level, proteinuria, a male gender, an elevated body mass index, an elevated cholesterol level, a smoking habit, and/or diabetes. Once a mammal having an elevated urinary CNP to plasma CNP ratio and one or more risk factors is identified, that mammal can be treated with one or more therapeutic agents designed to reduce or counter-act a symptom of a renal structural alteration. For example, a mammal having an elevated urinary CNP to plasma CNP ratio and hypertension can be treated with an ACE inhibitor, an angiotensin receptor blocker (ARB), an aldosterone antagonist, a statin, a native natriuretic peptide, or a designer natriuretic peptide to reduce a symptom of a renal structural alteration. In some cases, a mammal having an elevated urinary CNP to plasma CNP ratio and one or more risk factors can be instructed to self-treat with one or more therapeutic agents designed to reduce or counter-act a symptom of a renal structural alteration.

This document also provides methods and materials for treating a mammal that is likely to experience a poor outcome (e.g., death, hospitalization, heart failure, myocardial infarction, worsening renal function, worsening cardiac function, and dialysis). For example, a mammal can be assessed to determine if the mammal has an elevated level of urinary CNP or its six possible molecular forms (e.g., CNP-53 or NT-CNP-53). As described herein, mammals having an elevated level of urinary CNP or its six possible molecular forms (e.g., CNP-53 or NT-CNP-53) can be likely to experience a poor outcome. Once a mammal is identified as having an elevated level of urinary CNP or its six possible molecular forms (e.g., CNP-53 or NT-CNP-53), that mammal can be monitored for the presence of one or more risk factors of a poor outcome. For example, the mammal can be monitored or evaluated for the presence of an age factor, hypertension, an elevated serum creatinine level, proteinuria, a male gender, an elevated body mass index, an elevated cholesterol level, a smoking habit, and/or diabetes. Once a mammal having an elevated level of urinary CNP or its six possible molecular forms (e.g., CNP-53 or NT-CNP-53) and one or more risk factors is identified, that mammal can be treated with one or more therapeutic agents designed to reduce the likelihood of a poor outcome. For example, a mammal having an elevated level of urinary CNP or its six possible molecular forms (e.g., CNP-53 or NT-CNP-53) and hypertension can be treated with an ACE inhibitor, an ARB, an aldosterone antagonist, a statin, a native natriuretic peptide, or a designer natriuretic peptide to reduce the likelihood of a poor outcome. In some cases, a mammal having an elevated level of urinary CNP or its six possible molecular forms (e.g., CNP-53 or NT-CNP-53) and one or more risk factors can be instructed to self-treat with one or more therapeutic agents designed to reduce the likelihood of a poor outcome.

This document also provides methods and materials for treating mammals. For example, a mammal can be assessed to determine if the mammal has an elevated level of plasma CNP-22. As described herein, mammals having an elevated level of plasma CNP-22 can have an increased risk for death or myocardial infarction. Once a mammal is identified as having an elevated level of plasma CNP-22, that mammal can be monitored for the presence of one or more risk factors for death or myocardial infarction. For example, the mammal can be monitored or evaluated for the presence of an age factor, hypertension, an elevated serum creatinine level, proteinuria, a male gender, an elevated body mass index, an elevated cholesterol level, a smoking habit, and/or diabetes. Once a mammal having an elevated level of plasma CNP-22 and one or more risk factors is identified, that mammal can be treated with one or more therapeutic agents designed to reduce the mammal's risk of suffering from death or myocardial infarction. For example, a mammal having an elevated level of plasma CNP-22 and an elevated cholesterol level can be treated with an ACE inhibitor, an ARB, an aldosterone antagonist, a statin, a native natriuretic peptide, or a designer natriuretic peptide to reduce the mammal's risk of suffering from death or myocardial infarction. In some cases, a mammal having an elevated level of plasma CNP-22 and one or more risk factors can be instructed to self-treat with one or more therapeutic agents designed to reduce the mammal's risk of suffering from death or myocardial infarction.

The invention will be further described in the following examples, which do not limit the scope of the invention described in the claims.

EXAMPLES

Example 1—Use of Urinary CNP Excretion as Biomarker for Renal Fibrosis During Aging Animals Studies were performed in 2, 11, and 20 month old male Fischer rats (Harlan Laboratories, Inc., Madison, Wis., n=8-10 per age group, unless otherwise specified). The experimental study was performed in accordance with the Animal Welfare Act and with approval of the Mayo Clinic Institutional Animal Care and Use Committee.

Human Renal Biopsy Tissue

Human kidney tissue was obtained from core needle biopsy specimens from healthy living kidney donors at the time of kidney donation as described elsewhere (Rule et al., *Ann. Intern. Med.*, 152:561-567 (2010)). A total of six paraffin-embedded renal biopsy specimens were examined in this study. The young group consisted of three female donors with mean age of 19 years old (age range 18 to 20 years old) and old group consisted of three 71 year old female donors.

24 Hours Urine Collection

Rats were placed in metabolic cages with free access to food and water and acclimatized for 24 hours. Following the acclimatizing period, urine was then collected for 24 hours for proteinuria and CNP assessment. Urinary protein excretion was measured on 24 hour urine samples using the Pyrogallol Red dye-binding assay.

Acute Studies for Blood Pressure, Glomerular Filtration Rate, and Plasma Collection Rats were anesthetized (1.5% isoflurane in oxygen), and PE-50 tubing was placed into the carotid artery for blood pressure (BP) acquisition using CardioSOFT Pro software (Sonometrics Corporation, London, Ontario) and blood sampling. The bladder was cannulated for urine collection. The jugular vein was cannulated with PE-50 tubing and was continuously infused with 2% inulin (Sigma, St. Louis, Mo.) in normal saline. After 60 minutes of equilibration, a clearance study was performed. The clearance study lasted 60 minutes, and urine was collected with blood sampling at the end of the clearance study to calculate GFR from the clearance of inulin and for measuring plasma CNP. Blood was collected from the carotid artery and placed in EDTA tubes on ice (Stingo et al., *Am. J. Phys.*, 263:H1318-1321 (1992)). Blood was immediately centrifuged at 2,500 rpm at 4° C. for 10 minutes, and the plasma was stored in polystyrene tubes at −80° C. for future use. Inulin concentrations were measured using the anthrone method for GFR analysis as described elsewhere (Davidson and Sackner, *J. Lab. Clin. Med.*, 62:351-356 (1963)).

Rat Renal Tissue

After the acute study, the rat kidneys were removed for total weights and were then divided into sections. A cross-section of the renal tissue was preserved in 10% formalin for histological analysis of fibrosis and CNP, and smaller cube sections were preserved in 2.5% glutaraldehyde for electron microscopy (EM) analysis.

Histological Analysis of Fibrosis

Fixed rat renal tissues (n=7) were dehydrated, embedded in paraffin and sectioned at thickness of 4 µm. Collagen and extend of fibrosis was performed with picrosirius red staining. An Axioplan II KS 400 microscope (Carl Zeiss, Inc., Germany) was used to capture at least 4 randomly selected images from each slide using a 20× objective and KS 400 software was utilized to determined fibrotic area as a percentage of total tissue area.

Electron Microscopic Analysis

Rat renal tissues fixed in 2.5% glutaraldehyde were dehydrated and embedded in a resin mould. Ultra-thin sections were cut according to the EM core facility procedures. The glomeruli were imaged at 5000× and 8000× magnifications using a JEM-1400 transmission electron microscope.

Glomerular Basement Membrane Thickness Measurements

Glomerular EM images were captured at 5000× magnification from each age group (n=5) of rats. The thicknesses of the GBM were measured using the application Digital Micrograph (Gatan Inc., Pleasanton, Calif.). For each rat, 20 measurements were performed by an experienced EM technician and the data were subjected to an Excel morphometrics macro giving the mean thickness in nanometers (nm).

Plasma and Urinary CNP

Plasma and urinary CNP-22 was determined as described elsewhere (Stingo et al., *Am. J. Phys.*, 263:H1318-1321 (1992)) Using Commercially Available Non-equilibrium radioimmunoassay kits from Phoenix Pharmaceutical (Mountain View, Calif.) and an antibody to human CNP-22, which is fully cross-reactive to rat CNP-22. One mL of plasma was extracted using C-18 Bond Elut cartridges. After washing cartridges with 4 mL 100% methanol and 4 mL water, plasma was applied, and the cartridges were washed. Eluates were concentrated on a Savant speed vacuum concentrator, and pellets were re-suspended in 300 µL of assay buffer. 100 µL of standards and samples were incubated with 100 µL of anti-human CNP at 4° C. After 18 hours, 100 µL (10,000 counts) of $I^{125}$-labeled CNP was added and incubated at 4° C. for 18 hours. Then, a second antibody was added to all samples to separate the free and bound fractions, and the samples were centrifuged. The free fraction was aspirated, and the bound fraction was counted on a gamma counter. A standard curve was generated and used to calculate the concentrations of the unknown samples, which were reported in pg/mL. The range of the standard curve was 0.5 to 128 pg, with a lower limit of detection of 0.5 pg. Inter- and intra-assay variability was 11% and 5.2%, respectively. Recovery was 72±6%. Cross-reactivity was <1% with ANP, BNP, endothelin, and adrenomedullin, and 97% with CNP-53.

CNP Immmunohistochemistry

The presence of renal CNP immunoreactivity was assessed as described elsewhere (Stingo et al., *Am. J. Phys.*, 263:H1318-1321 (1992)). Briefly, slides with paraffin-embedded renal tissues were incubated in a 60° C. oven for 2 hours and then deparaffinized using established laboratory procedures. After deparaffinization, slides were incubated with 0.6% hydrogen peroxide in methanol for 20 minutes at room temperature to block endogenous peroxidase activity, and then 5% normal goat serum was used to block nonspecific protein binding sites before primary antibody was applied. Sections were placed in a moist chamber for 18-24 hours at room temperature with the primary antibody (rabbit anti-human CNP-22, Phoenix Pharmaceutical, Mountain View, Calif.) at a dilution of 1:500. Control slides were treated with normal rabbit serum. Sections were incubated with goat anti-rabbit IgG covalently linked to horseradish peroxidase and 3-amino-9-ethyl-carbazole substrate for peroxidase visualization and were counterstained with hematoxylin to enhance nuclear detail. Staining slides were then viewed and interpreted by a renal pathologist blinded to the age groups.

Statistical Analysis

Results were expressed as mean±SE. Comparisons within groups were made by ANOVA followed by Newman-Keuls multiple comparison test. A Pearson correlation was performed to calculate the correlation between urinary CNP excretion and renal fibrosis as well as GFR and between the urinary to plasma CNP ratio and renal fibrosis. GraphPad Prism software (GraphPad Software, La Jolla, Calif.) was used for the above calculations. Statistical significance was accepted as $P<0.05$.

Results

Anthropometric, Renal Characteristics, and Hemodynamics with Aging

Body weight (BW), total kidney weight (TKW), plasma creatinine, GFR as well as mean arterial pressure (MAP) levels were determined (Table 1). There was a significant increase in BW and TKW at 11 months, which was sustained at 20 months as compared to the 2 month old group. When TKW was normalized to BW, there was a significant reduction in the TKW:BW ratio at 11 and 20 months of age. Further, while plasma creatinine was significantly increased at 11 and 20 months compared to 2 month of age, there was a trend for GFR to decrease at 11 months, which was sustained at 20 months. There was a significant elevation in MAP only at 20 months of age.

TABLE 1

Summary of body weight, renal characteristics, and blood pressure in aging Fischer rats.

|  | 2 months | 11 months | 20 months |
| --- | --- | --- | --- |
| BW (g) | 211 ± 2 | 465 ± 5* | 445 ± 7*† |
| TKW (mg) | 1614 ± 33 | 2763 ± 73* | 2750 ± 54* |
| TKW:BW (mg/g) | 7.67 ± 0.19 | 5.94 ± 0.15* | 6.18 ± 0.13* |
| Plasma Cr (mg/dL) | 0.20 ± 0.00 | 0.39 ± 0.03* | 0.36 ± 0.02* |
| GFR (mL/min/kg) | 3.52 ± 0.29 | 2.61 ± 0.43 | 2.83 ± 0.30 |
| MAP (mmHg) | 90 ± 1 | 91 ± 2 | 100 ± 3*† |

BW = body weight;
TKW = total kidney weight;
Cr = creatinine;
GFR = glomerular filtration rate;
MAP = mean arterial pressure.
Values are mean ± SE.
n = 10 for all age groups.

*$P < 0.05$ vs 2 months, †$P < 0.05$ vs. 11 months.

Renal Fibrosis and Glomerular Ultrastructure

Figure 1A:
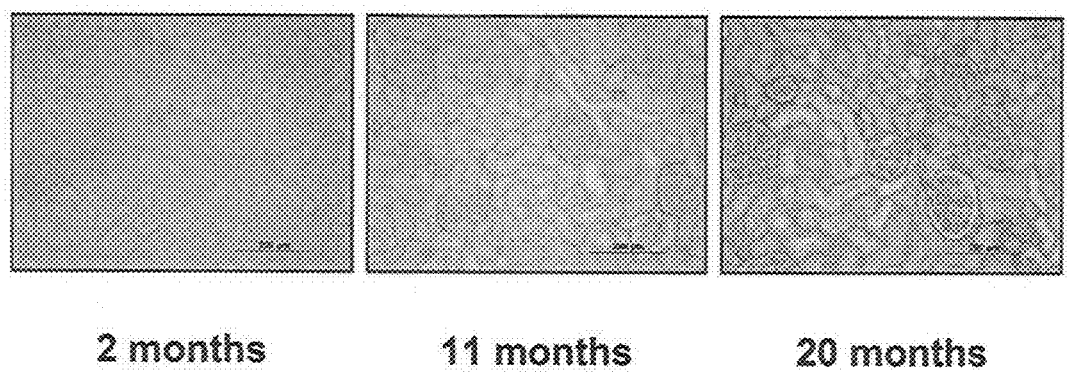
FIGS. 1A-B. Representative histology images at 20× objective magnification (A) and quantification of picrosirius red staining (B) of renal cortical fibrosis from 2, 11, and 20 month old Fischer rats. Values are mean±SE. n=7 for all age groups. *P<0.05 vs. 2 months, †P<0.05 vs. 11 months.
Figure 1B:
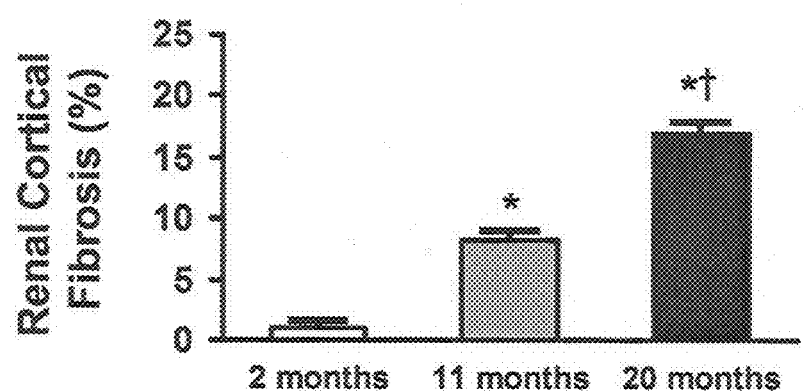
Figure 2A:
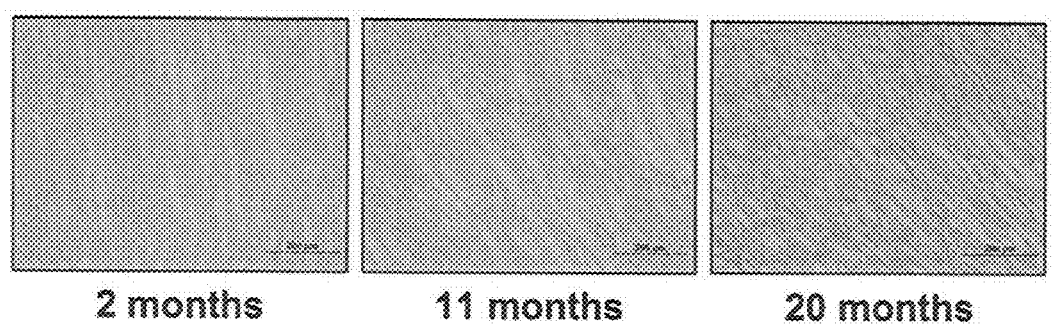
FIGS. 2A-B. Representative histology images at 20× objective magnification (A) and quantification of picrosirius red staining (B) of renal medullary fibrosis from 2, 11, and 20 month old Fischer rats. Values are mean±SE. n=7 for all age groups. *P<0.05 vs. 2 months, †P<0.05 vs. 11 months.
Figure 2B:
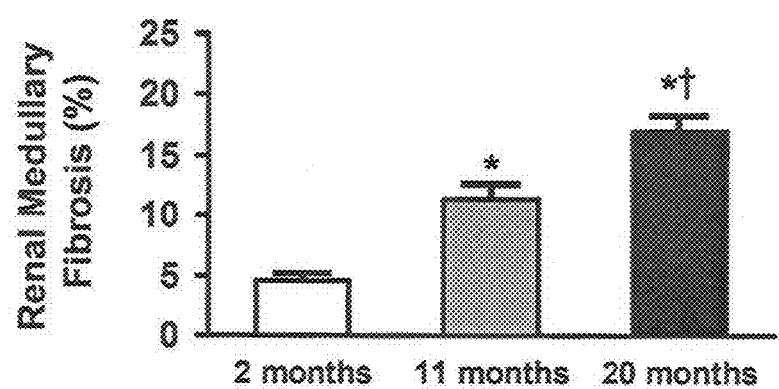
Figure 3A:
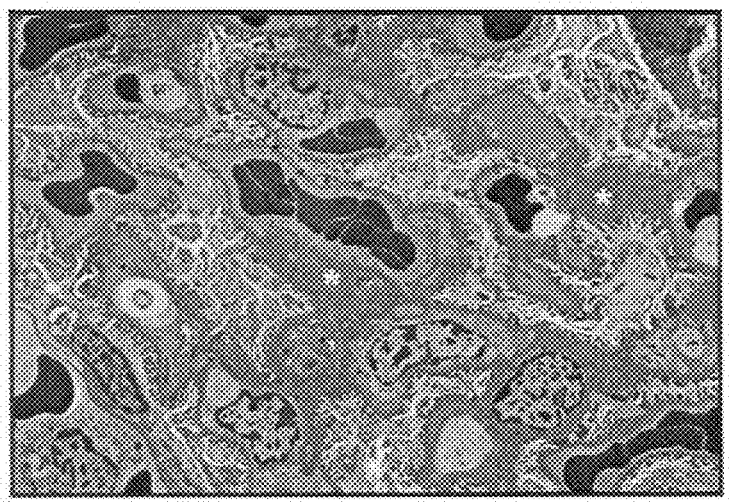
FIGS. 3A-C. Representative electron micrographs at 8000× magnification of the glomerulus from 2 (A), 11 (B), and 20 (C) month old Fischer rats.
Figure 3B:
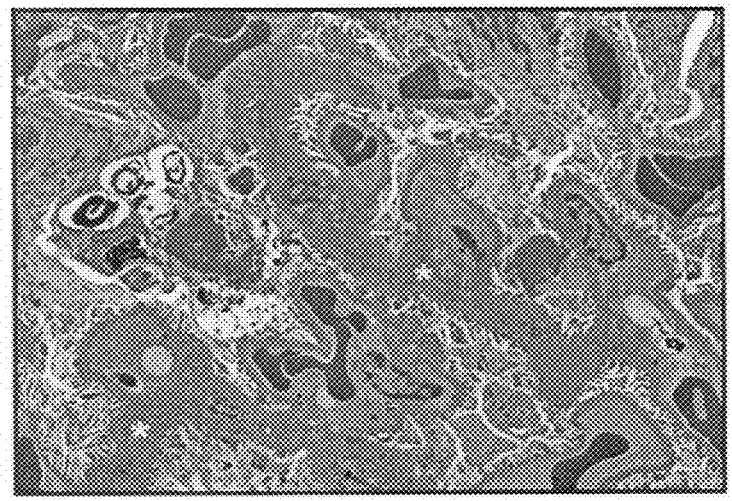
Figure 3C:
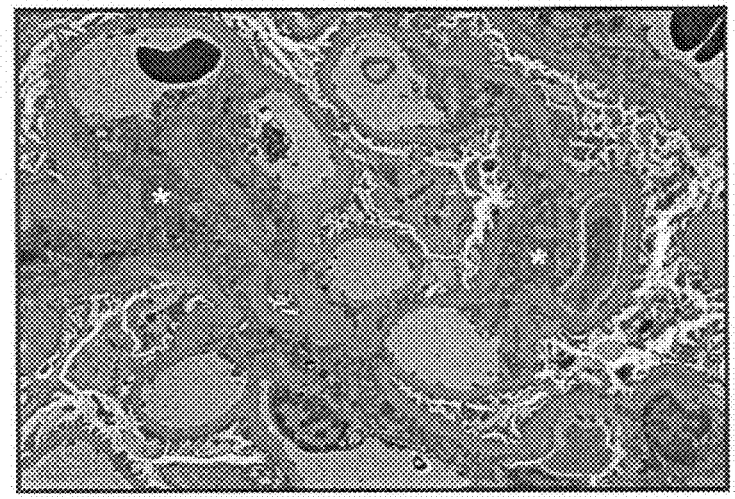
Figure 4:
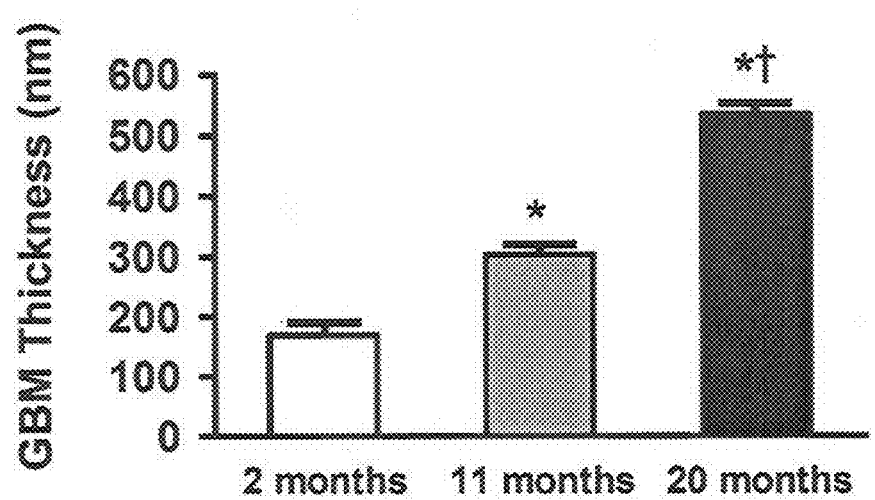
FIG. 4. Quantification of glomerular basement thickness from 2, 11, and 20 month old Fischer rats. Values are mean±SE. n=5 for all age groups. *P<0.05 vs. 2 months, †P<0.05 vs. 11 months.

Representative photomicrographs of the renal cortex (FIG. 1A) and medulla (FIG. 2A) stained with picrosirius red were obtained. These photomicrographs provided an estimate of fibrillar collagen deposition. Specifically, there was a significant and progressive increase in cortical (FIG. 1B) and medullary (FIG. 2B) interstitial collagen staining with aging. Further, representative electron photomicrographs of glomeruli were obtained (FIG. 3). At 2 months (FIG. 3A), visceral epithelial cell foot processes were intact. At 11 months (FIG. 3B), mesangial regions were mildly expanded with matrix, and the capillary loop basement membranes exhibited mild thickening compared to 2 months. At 20 months (FIG. 3C), there was diffuse expansion of mesangial matrix. The capillary loop basement membranes were thickened and exhibited focal effacement of visceral epithelial cell foot processes as compared 2 and 11 months of age. Morphometric analysis of GBM thickness was performed (FIG. 4). There was progressive and significant thickening of capillary loop basement membranes with aging, where the thickness of basement membranes at 20 months was almost three times that of the basement membranes at 2 months of age.

Immunohistochemical Localization of Renal CNP

Immunohistochemical localization of CNP in the renal cortex (left column panels) and the medulla (right column panels) was evaluated in Fischer rats at 2, 11, and 20 months of age (FIG. 5). At 2 months of age, there was no significant staining of proximal tubules, and immunostaining for CNP was localized to distal tubules within the renal cortex. At 11 months of age, CNP immunostaining within renal cortex was predominantly localized to distal tubules, with faint staining of proximal tubules. At 20 months, strong immunostaining for CNP was observed within distal tubules and focally, within proximal tubules of the renal cortex. Strong immunostaining for CNP was observed within distal tubules of the renal medulla and did not appreciably change with age.

Figure 10:
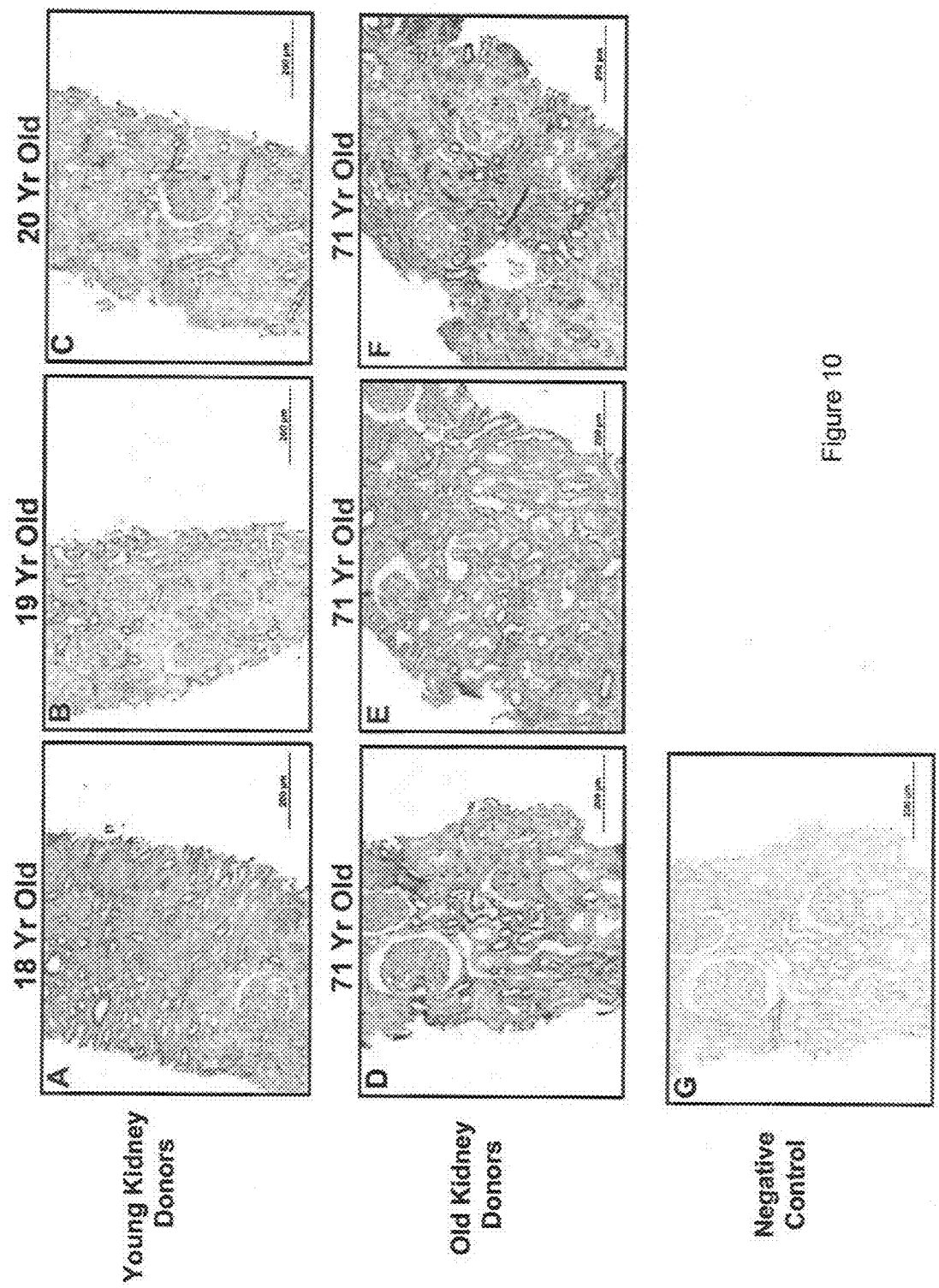
FIG. 10. CNP immunohistochemical localization in renal tissue from young human donors (A-C) and old human donors (D-F) at 20× objective magnification. Negative control (G).
Figure 13B:
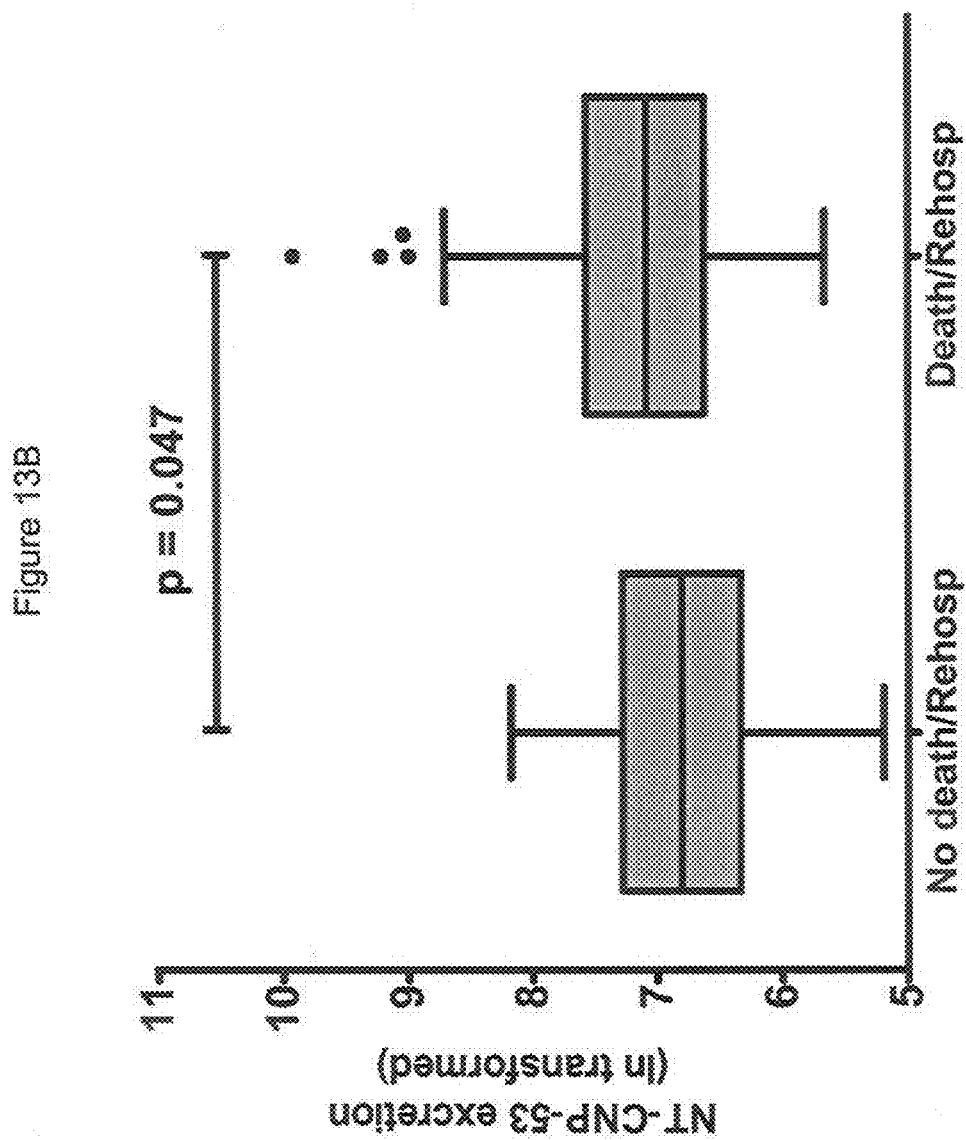
Figure 14B:
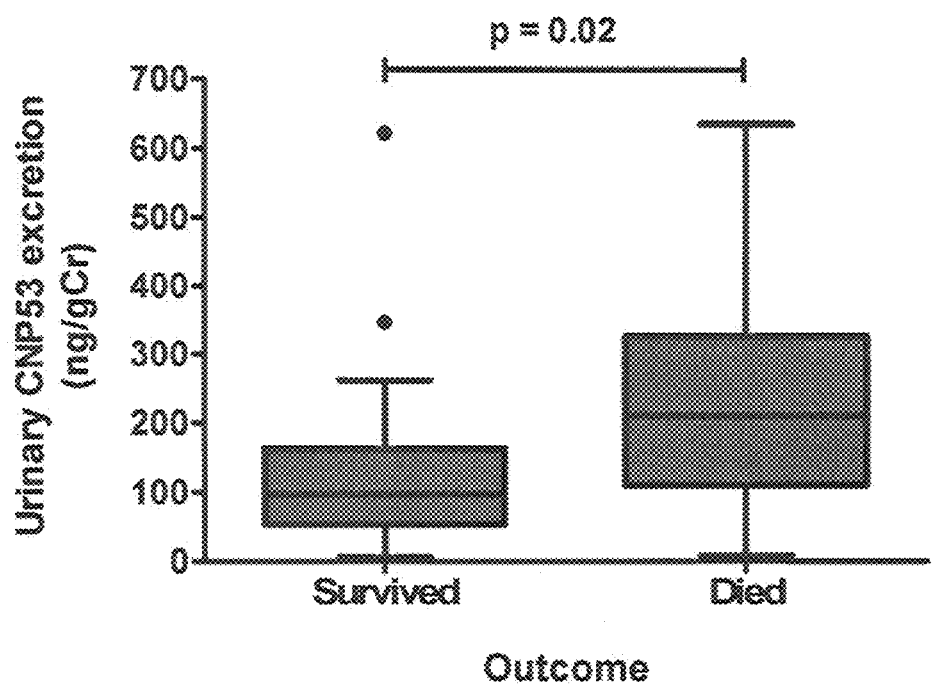
Figure 14C:
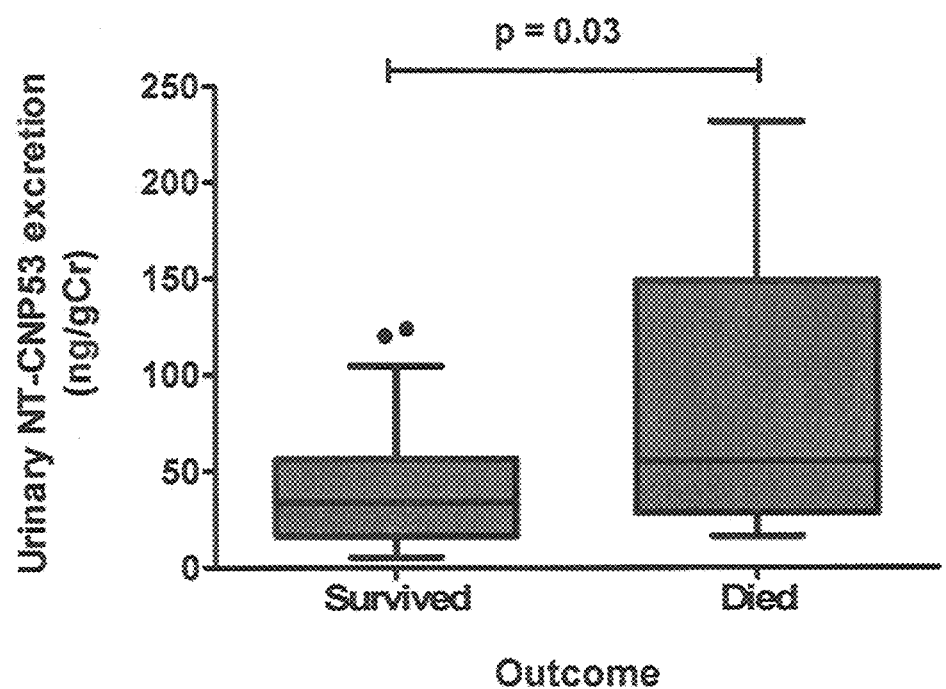

Additionally, FIG. 10 demonstrates immunohistochemical localization of CNP in young (A-C) and old (D-F) biopsy specimens from healthy human kidney donors. In biopsies obtained from young kidney donors, CNP staining was predominantly localized to distal tubules, with relatively weak, focal staining observed within proximal tubules. In biopsies obtained from old kidney donors (D-F), strong staining of CNP was observed within both distal and proximal tubules.

Urinary and Plasma CNP, Urinary to Plasma CNP Ratio, and Proteinuria

Changes in plasma and urinary CNP with aging were assessed (FIG. 6). A significant and progressive decrease in plasma CNP (FIG. 6A) was observed between the three age groups (2 month mean±SE: 29±3 pg/mL; 11 month mean±SE: 20±1*pg/mL; 20 month mean±SE: 9±1*† pg/mL; *P<0.05 vs. 2 months, † P<0.05 vs. 11 months). In contrast, there was a significant increase in urinary CNP excretion at 11 months, which remained elevated at 20 months (2 month mean±SE: (64±4 pg/day; 11 month mean±SE: 110±6*pg/day; 20 month mean±SE: 103±7*pg/day; *P<0.05 vs. 2 months) (FIG. 6B). Further, there also was a significant and progressive increase in the urinary to plasma to CNP ratio (FIG. 6C: 2 month mean±SE:2.2±0.2 pg/day/pg/mL; 11 month mean±SE: 5.4±0.3*pg/day/pg/mL; 20 month mean±SE: 11.7±1.0*† pg/day/pg/mL; *P<0.05 vs. 2 months, † P<0.05 vs. 11 months). A significant increase in proteinuria (FIG. 6D) was observed only at 20 months.

Urinary CNP Excretion and Urinary to Plasma CNP Ratio Correlations

Figure 7B:
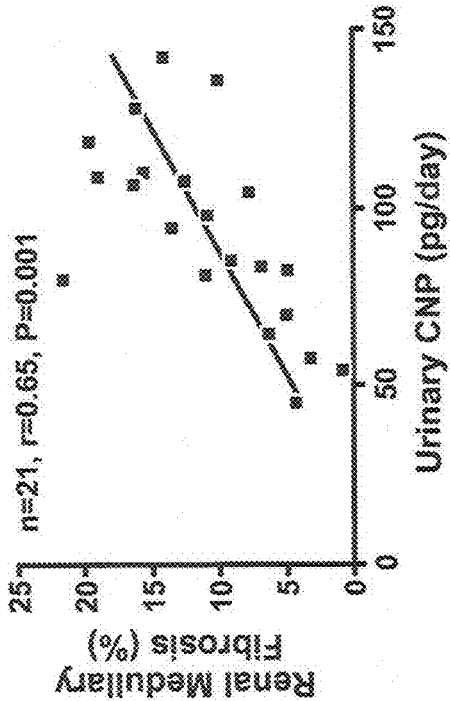
FIGS. 7A-D. Correlations between urinary CNP excretion and renal cortical (A) and medullary (B) fibrosis, as well as between urinary to plasma CNP ratio and renal cortical (C) and medullary (D) fibrosis.
Figure 7D:
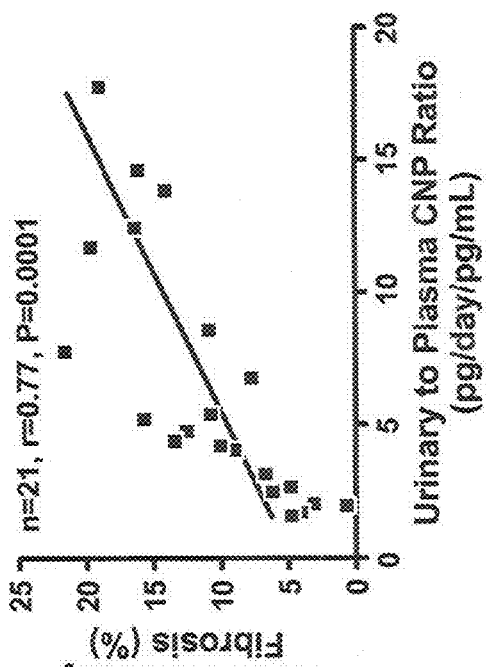
Figure 7A:
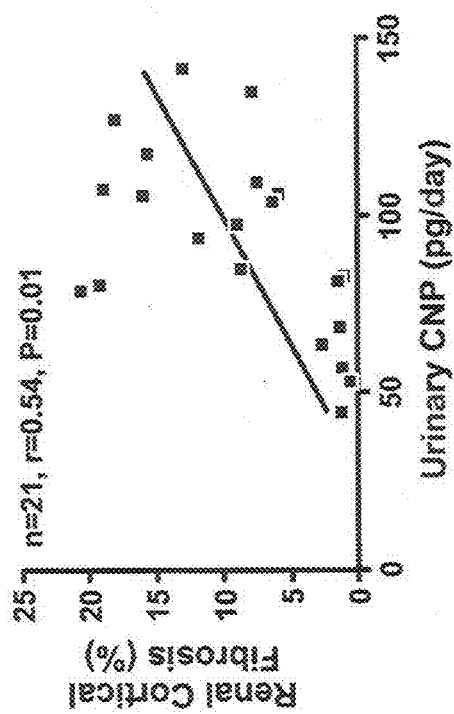
Figure 7C:
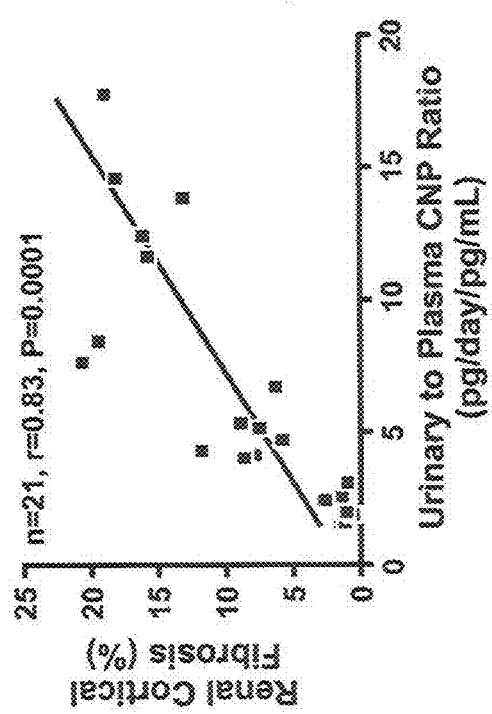

A positive correlation was revealed between CNP and renal cortical fibrosis (FIG. 7A; n=21, r=0.54, P=0.01), and between CNP and renal medullary fibrosis (FIG. 7B; n=21, r=0.65, P=0.001). Further, there was a strong positive correlation between a urinary to plasma CNP ratio and renal cortical fibrosis (FIG. 7C; n=21, r=0.83, P=0.0001), and between a urinary to plasma CNP ratio and renal medullary fibrosis (FIG. 7D; n=21, r=0.77, P=0.0001). There was no correlation between urinary CNP and GFR (n=30, r=0.01, P=0.97). FIG. 11 illustrates a strong positive correlation among GBM thickness, urinary CNP (FIG. 11A; n=15, r=0.77, P=0.0008) and urinary to plasma CNP ratio (FIG. 11B; n=15, r=0.95, P=0.0001).

The results provided herein demonstrate that urinary CNP excretion increases during aging and that increased urinary CNP excretion is strongly associated with renal fibrosis and GBM thickening, which occurred prior to the onset of significant proteinuria or BP elevation. The increase in urinary CNP excretion observed with renal aging occurred together with a significant increase in the urinary to plasma CNP ratio and decrease in circulating CNP and renal function. These results demonstrate that urinary CNP and its ratio with plasma CNP is a biomarker for early renal structural changes during aging prior to the appearance of clinical signs.

Example 2—CNP is a Urinary Biomarker with Prognostic Value in Hospitalized Acute Decompensated Heart Failure (ADHF) Patients Independent of Glomerular Filtration Rate and NT-proBNP Patient Population Sixty ADHF (acute decompensated heart failure) patients were studied, and 20 healthy subjects were included as the control group. ADHF patients were prospectively identified and enrolled from a register of consecutive admissions. Inclusion criteria were a clinical diagnosis of systolic HF consistent with Framingham criteria (McKee et al., *N. Engl. J. Med.*, 285:1441-6 (1971)) for either new onset or established chronic HF, confirmed by reduced (<50%) left ventricular ejection fraction (LVEF) on echocardiography. In order that the study population may reflect the heterogeneity of normal clinical practice, the only exclusion criterion was incomplete or incorrect urine collection for adequate urinary biomarker analysis. Two ADHF patients were excluded for this reason, leaving a total of 58 consecutive patients providing consent in the ADHF cohort. All patients underwent baseline history assessment, physical examination, and transthoracic echocardiography as part of routine clinical care. Plasma samples for CNP and NT-proBNP measurements and 24 hour urine collection were also obtained within 72 hours of admission. Urine samples were collected on ice with acetic acid (30 mL of 1:1 acetic acid; 17.4 M). At the end of the timed urine collection (mean 22.9±4 hours), total volume was recorded, and samples aliquoted from each container, frozen and stored at −80° C. until analysis. For the preliminary analysis, GFR was defined as 24 hour creatinine clearance. Results were retrospectively verified to concur with modified diet in renal disease (MDRD) estimates of GFR.

Control subjects were recruited from a population of healthy volunteers. All were non-smokers and had no history of cardiovascular or systemic disease. Plasma samples for CNP and NT-proBNP measurements and 24-hour urine collections were obtained upon enrollment.

Urine Biomarker Assays

NGAL and KIM-1

Urine concentrations of NGAL and KIM-1 were measured by enzyme-linked immunoassay as per manufacturer's instructions (Quantikine® ELISA, R&D Systems). The minimum detectable dose for NGAL was 0.012 ng/mL, and the minimum detectable dose for KIM-1 was 0.009 ng/mL.

The intra- and inter-assay coefficient of variation for both assays were <5% and <8%, respectively. NGAL is recognized to form complexes with MMP9; recombinant human MMP-9/NGAL complex demonstrated 0.3% cross-reactivity in the assay used. There was no significant cross-reactivity or interference in the KIM assay.

CNP-22 (AA 82-103)

Urinary CNP-22 was determined by commercially available non-equilibrium radioimmunoassay kits from Phoenix Pharmaceutical (Mountain View, Calif.), using an antibody that detects human CNP-22 as described elsewhere (Sangaralingham et al., Am. J. Physiol. Renal Physiol., 301:F943-52 (2011)). The range of the standard curve was 0.5-128 pg, with a lower limit of detection of 0.5 pg. Inter- and intra-assay variability was 11% and 5%, respectively. Recovery was 85%. Cross-reactivity was 0% with ANP, BNP, endothelin, and NT-CNP53, and 59% with CNP-53.

CNP-53 (AA 51-103) and NT-CNP53 (AA 51-81)

Urinary CNP-53 and NT-CNP-53 were determined, similar to that of CNP-22, by commercially available non-equilibrium radioimmunoassay kits from Phoenix Pharmaceutical (Mountain View, Calif.), using antibodies that detect human CNP-53 (CNP-53) and the first 29 amino acids of CNP-53 starting from the amino-terminal only when it is separated from the ring structure (NT-CNP-53). A standard curve was generated and used to calculate the concentrations of the unknown samples and reported in pg/mL. For CNP-53, the range of the standard curve was 0.5-128 pg. Inter- and intra-assay variability was 8% and 7%, respectively. Recovery was 81±4%. Cross reactivity was 100% with CNP-22 and 0% with NT-CNP-53, ANP, and BNP. For NT-CNP-53, the range of the standard curve was 0.5-128 pg. Inter- and intra-assay variability was 10% and 6%, respectively. Recovery was 82±5.2%. Cross-reactivity was 0% with ANP, BNP, CNP-22, CNP-53, and endothelin.

Urine Biomarker Excretion

Mean urine flow (mL/hour) was determined from total urine volume (mL) and urine collection time (hours). Urine biomarker excretion was calculated as the product of urine biomarker concentration (pg/mL or ng/mL) and urine flow rate (mL/hour) and reported following adjustment for urinary creatinine excretion (ng/gCr).

Plasma Biomarker Assays

Blood was drawn into EDTA tubes and chilled until centrifuged at 4° C., 2500 rpm, for 10 minutes. 1 mL plasma was aliquoted and frozen at −20° C. until assayed. Plasma concentrations of CNP molecular forms were determined using the same non-equilibrium RIA utilized for urine (Phoenix Pharmaceuticals, Belmont, Calif.); using anti-human CNP antibodies. Plasma NT-proBNP was measured by electrochemiluminescence immunoassay as previously described elsewhere (Costello-Boerrigter et al., J. Am. College Cardiol., 47:345-53 (2006)). The lower limit of detection for NT-proBNP was 5 pg/mL; inter-assay and intra-assay variability was 3.1% and 2.5%, respectively. There was no cross-reactivity with CNP forms.

Statistical Analysis

All urinary biomarkers demonstrated a non-Gaussian distribution; therefore, values are presented as median±interquartile range. For comparisons between ADHF and control subjects, non-parametric Wilcoxon rank-sum tests were used. Spearman's rank correlation was used to ascertain relationships between continuous variables. Biomarker excretion data was normalized by natural logarithmic transformation prior to Cox regression analysis to detect independent predictors of: (i) mortality, and (ii) time to first non-elective all-cause rehospitalization/death. Mortality and rehospitalization were ascertained from institutional records, which included local primary care data. Patients were otherwise censored at time of last known follow-up. C-statistics were used to compare the discriminatory ability of biomarkers (Harrell et al., Statistics in medicine, 15:361-87 (1996)). The c-statistic is similar to the area under the curve for binary endpoints and can be interpreted as the probability of correctly ordering event times using risk score from the Cox model. Confidence intervals were calculated for c-statistics using an approximate jackknife method of calculating standard errors. Additionally, the integrated discrimination index (IDI) (Pencina et al., Statistics in medicine, 27:157-72 (2008); discussion 207-12) was utilized to evaluate the improvement in predictive accuracy using the combination of CNP and plasma NT-proBNP over the use of NT-proBNP alone, for adverse outcomes (mortality and rehospitalization/death) in ADHF. Probability values were 2-sided; p<0.05 was considered significant. Data were analyzed using JMP software version 9.0 (SAS Institute, Inc., Cary, N.C.) and SAS version 9.2 (SAS Institute, Inc., Cary, N.C.).

Results

Baseline clinical and biochemical characteristics of the study population are shown in Table 2. Patients admitted with ADHF were older than controls (70.1±10.3 vs. 53.5±6.1 years; p<0.0001), 23 (40%) were female; and mean left ventricular ejection fraction (LVEF) was 38.4±18.9%. Twenty two (38%) ADHF patients presented with dyspnea alone as the predominant symptom; 4 patients (7%) presented with edema alone; and 24 (41%) presented with combined dyspnea and peripheral edema. The remaining few patients presented with fatigue or ADHF in the context of arrhythmia-related symptoms. Fifty five percent presented in NYHA Class III. Plasma NT-proBNP was significantly elevated in ADHF patients, while GFR was reduced compared to controls (p<0.0001) (Table 2). Urinary creatinine concentration was observed to be lower in ADHF than controls (Table 3), likely in accordance with instigation or escalation of diuretic therapy during clinical ADHF management.

TABLE 2

Baseline characteristics.

| Variable | Control (n = 20) | ADHF (n = 58) | p-value |
|---|---|---|---|
| Age*, y | 53.5 ± 6.1 | 70.1 ± 10.4 | <0.0001 |
| Male gender, n (%) | 10 (50) | 35 (59) | 0.50 |
| Ischemic etiology, n (%) | — | 19 (33) | — |
| Co-morbidity | | | |
| Hypertension, n (%) | — | 36 (62) | — |
| Diabetes, n (%) | — | 25 (43) | — |
| Thyroid disease, n (%) | — | 11 (19) | — |
| Atrial fibrillation, n (%) | — | 38 (66) | — |
| Previous CVA, n (%) | — | 7 (12) | — |
| CRT, n (%) | — | 14 (24) | — |
| Medications on admission | | | |
| ACEI or ARB, n (%) | — | 38 (66) | — |
| Beta-blocker, n (%) | — | 44 (76) | — |
| Loop diuretic, n (%) | — | 49 (84) | — |
| Aldosterone antagonist, n (%) | — | 12 (21) | — |

TABLE 2-continued

Baseline characteristics.

| Variable | Control (n = 20) | ADHF (n = 58) | p-value |
|---|---|---|---|
| Mean LVEF*, % | — | 38.0 ± 18.9 | — |
| Serum creatinine*, mg/dL | 0.7 ± 0.18 | 1.2 ± 0.8 | <0.0001 |
| GFR*, ml/min/1.73 m² | 115.9 ± 21.1 | 60.5 ± 30.3 | <0.0001 |
| Plasma biomarkers (pg/ml)µ | | | |
| NT-proBNP | 37.8 (21.9-67.3) | 2461 (1222-6994) | <0.0001 |
| CNP-22 | 6.4 (4.3-18.8) | 11.7 (8.3-19.6) | 0.005 |
| CNP-53 | 3.8 (3.6-4.3) | 5.8 (5.0-7.6) | 0.0001 |
| NT-CNP-53 | 6.5 (5.4-7.7) | 6.1 (5.3-6.9) | 0.56 |

*Values expressed as mean (SD)

µValues expressed as median (25th-75th percentile).

CVA, cerebrovascular accident;

CRT, cardiac resynchronization therapy;

LVEF, left ventricular ejection fraction;

GFR, glomerular filtration rate;

NT-proBNP, N-terminal pro-brain natriuretic peptide;

CNP-22, C-type natriuretic peptide-22;

CNP-53, C-type natriuretic peptide-53;

NT-CNP-53, N-terminal fragment of C-type natriuretic peptide -53.

Acute Decompensated Heart Failure and Urinary Biomarker Excretion

Excretion rates for all urinary biomarkers displayed a non-Gaussian distribution. Median excretion of KIM-1 and all three CNP molecular forms was significantly higher in ADHF than controls, as was the urinary total protein/creatinine ratio (Table 3 and FIG. 12). Urinary NGAL excretion was unchanged (p=NS). Associations between urinary biomarker excretion and clinical characteristics of ADHF patients were explored. KIM-1 demonstrated a weak non-significant association with GFR (Spearman's ρ −0.19; p=0.098), but there were no significant relationships between any urinary biomarker and NYHA class (III or IV) at presentation, nor any significant trends associated with LVEF (off inotropes) (p=NS for both).

Univariate correlation coefficients between excretion rates of urinary CNP and other measured HF biomarkers are shown in Table 4. Moderate correlations were observed between the three urinary CNP molecular forms but only urinary CNP-22 displayed any, albeit modest, correlation with its concentration in the plasma (ρ 0.28, p=0.04). Urinary CNP-22 and CNP-53 were weakly associated with plasma NT-proBNP (ρ 0.45, p=0.0003; ρ 0.33, p=0.01 respectively); urinary NT-CNP-53 was not. Urinary CNP-22 (ρ 0.68, p=0.0001) and urinary KIM-1 (ρ 0.78, p<0.0001) demonstrated a marked correlation with urinary total protein/creatinine ratio which was not evident with the other urinary biomarkers: CNP-53, NT-CNP-53 or NGAL.

Amongst ADHF patients, medications on admission included angiotensin converting enzyme inhibitors or angiotensin-receptor blockers (66%), β blockers (76%), loop diuretics (84%), and aldosterone antagonists (21%). On exploratory analysis, urinary NGAL was higher in the context of ACEI or ARB use (median±IQR: 443±1924 vs. 177±227 ng/gCr; p=0.003), and urinary NT-CNP-53 was lower in ADHF patients admitted on loop diuretics (34.0±43.7 vs. 60.4±202.0; p=0.01) than those without. No other significant associations were observed between use of these agents on presentation and urine CNP-22, CNP-53, or KIM-1 levels in the current cohort.

TABLE 3

Urinary biomarker excretion.

| | Control (n = 20) | ADHF (n = 58) | p-value |
|---|---|---|---|
| Urine volume* (mL) | 1878.0 (653.7) | 1824.8 (1129.3) | 0.80 |
| Urine collection time* (h) | 24.0 (0) | 22.9 (4.0) | 0.05 |
| Urinary creatinine* (mg/dL) | 75.5 (38.1) | 55.3 (37.8) | 0.04 |
| Urine protein/creatinine ratio (mg/mg)§ | 0.02 (0.01-0.02) | 0.03 (0.02-0.08) | 0.0007 |
| Biomarker excretion (ng/gCr)§ | | | |
| KIM-1 | 475.0 (198.9-604.9) | 1354.0 (876.5-2101.5) | <0.0001 |
| NGAL | 298.8 (225.2-458.3) | 350.2 (137.2-1405.7) | 0.94 |
| CNP-22 | 7.2 (6.7-9.6) | 14.0 (8.1-27.0) | 0.0003 |
| CNP-53 | 64.7 (21.6-109.1) | 115.2 (63.1-227.8) | 0.02 |
| NT-CNP-53 | 19.4 (13.3-29.6) | 35.8 (20.0-72.6) | 0.0015 |

*Values expressed as mean (SD)

§Values expressed as median (25th-75th percentile)

KIM-1, kidney injury molecule 1;

NGAL, neutrophil gelatinase-associated lipocalin;

CNP-22, C-type natriuretic peptide-22;

CNP-53, C-type natriuretic peptide-53;

NT-CNP-53, N-terminal fragment of C-type natriuretic peptide -53.

TABLE 4

Correlation analysis: Spearman's ρ (rho) rank correlation between CNP molecular forms and other potentially important biomarkers of disease severity or prognosis in ADHF patients.

| | Urine CNP-22 | | Urine CNP-53 | | Urine NT-CNP-53 | |
|---|---|---|---|---|---|---|
| | ρ | p-value | ρ | p-value | ρ | p-value |
| Age | 0.04 | 0.74 | 0.08 | 0.57 | 0.06 | 0.65 |
| GFR | −0.11 | 0.41 | 0.08 | 0.53 | 0.27 | 0.04 |
| Urine total protein/creatinine ratio | 0.68 | 0.0001 | −0.42 | 0.06 | 0.04 | 0.85 |
| Urinary biomarkers | | | | | | |
| KIM-1 | 0.19 | 0.16 | 0.30 | 0.02 | 0.21 | 0.11 |
| NGAL | 0.43 | 0.0007 | 0.12 | 0.36 | 0.07 | 0.61 |
| CNP-22 | 1 | — | 0.66 | <0.0001 | 0.50 | <0.0001 |
| CNP-53 | 0.66 | <0.0001 | 1 | — | 0.58 | <0.0001 |
| NT-CNP-53 | 0.50 | <0.0001 | 0.58 | <0.0001 | 1 | — |
| Plasma biomarkers | | | | | | |
| CNP-22 | 0.28 | 0.04 | 0.24 | 0.07 | 0.26 | 0.05 |
| CNP-53 | 0.12 | 0.39 | −0.08 | 0.52 | −0.12 | 0.38 |
| NT-CNP-53 | −0.08 | 0.58 | 0.09 | 0.53 | −0.14 | 0.31 |
| NT-proBNP | 0.45 | 0.0003 | 0.33 | 0.01 | 0.09 | 0.53 |

GFR, glomerular filtration rate;
KIM-1, kidney injury molecule 1;
NGAL, neutrophil gelatinase-associated lipocalin;
CNP-22, C-type natriuretic peptide-22;
CNP-53, C-type natriuretic peptide-53;
NT-CNP-53, N-terminal fragment of C-type natriuretic peptide -53;
NT-proBNP, N-terminal pro-brain natriuretic peptide.

Plasma Concentrations of C-Type Natriuretic Peptide

Plasma concentrations of CNP molecular forms and NT-proBNP are shown in Table 2. Plasma CNP-22 and CNP-53 were elevated in ADHF compared to controls, whereas plasma NT-CNP-53 was unchanged. Plasma CNP-22 demonstrated limited association to its concurrent urine excretion (ρ 0.28, p=0.04), and a weakly positive trend with urine CNP-53 (ρ 0.24, p=0.07) and NT-CNP-53 excretion (ρ 0.26, p=0.05) (Table 4). By contrast, neither plasma CNP-53 nor plasma NT-CNP-53 displayed any relationship to urinary excretion of any CNP molecular form.

Clinical Outcomes

Of the 58 ADHF patients studied, there were 18 deaths (overall ADHF mortality 31%) over a mean (SD) follow-up of 1.5 (0.9) years. Eighteen additional ADHF patients were rehospitalized (all-cause rehospitalization/death rate 62%) of which 13 patients were rehospitalized with a primary presenting complaint of cardiovascular etiology. Two patients were admitted for elective cardiac resynchronization therapy procedures; these were not included as events in the final analysis.

ADHF patients who died were older than survivors (74.8±9.2 vs. 67.9±10.2 years, p=0.02) but were otherwise similar with respect to gender, NYHA class, and LVEF. Likewise, ADHF patients who met the secondary outcome of all-cause rehospitalization/death during follow up were not different from ADHF patients without events in respect to these baseline characteristics. Neither plasma NT-proBNP nor GFR were significantly different between ADHF patients with or without adverse outcomes in this cohort. Of the urinary biomarkers assessed, all three CNP forms were elevated in ADHF patients who died compared to survivors (FIGS. 13A-C and 14A-C). Urinary KIM-1 and NGAL excretion were unchanged (p=NS for both). Plasma CNP-22 was higher in ADHF patients who died than survivors (15.8±18.8 vs. 10.5±8.3 pg/mL; p=0.02), but plasma CNP-53 and NT-CNP-53 not significantly different. For patients who met the secondary outcome, urinary CNP-22 and NT-CNP-53 excretion displayed a trend towards elevation (median CNP-22: 15.3 vs. 9.3 ng/gCr, p=0.07; NT-CNP-53: 37.4 vs. 32.6 ng/gCr, p=0.06) as did plasma CNP-22 (13.8±16.3 vs. 10.5±7.7; p=0.06). The remaining urinary biomarkers and plasma CNP forms were unchanged.

Cox regression analysis (Table 5) revealed only urinary NT-CNP-53 excretion to be significantly predictive of mortality (univariate HR 1.67, 95% CI 1.14-2.37, p=0.01) and all-cause rehospitalization/death (univariate HR 1.78, 95% CI 1.30-2.39, p=0.0004) from all urinary and plasma biomarkers assessed. Moreover, its association persisted after adjusting for age, urinary protein/creatinine ratio, and plasma NT-proBNP (Table 5). On analysis of the c-statistic (c-index) for the occurrence of all-cause mortality, urinary NT-CNP-53 displayed a comparable c-statistic (0.66; 95% CI 0.53-0.78) to that of NT-proBNP (0.57, 95% CI 0.43-0.71), and the combination of biomarkers, urinary NT-CNP-53 and plasma NT-proBNP, provided evidence of an incremental effect with a combined c-statistic of 0.69 (95% CI 0.56-0.82). Examination of the integrated discrimination index provided further evidence that the combination of urinary NT-CNP-53 and plasma NT-proBNP significantly improved prediction of adverse outcomes in this cohort (Table 6). No other urinary or plasma biomarker in this study demonstrated significant predictive value.

TABLE 5

Predictive value of urinary NT-CNP-53 excretion and plasma NT-proBNP for clinical outcome in ADHF patients. Univariate and adjusted Cox proportional hazard analysis.

| | Outcome | | | |
|---|---|---|---|---|
| | Death | | All-cause re-hospitalization/death | |
| Model | HR (95% CI) | p-value | HR (95% CI) | p-value |
| Urinary NT-CNP 53* | | | | |
| Unadjusted | 1.67 (1.14-2.37) | 0.01 | 1.78 (1.30-2.39) | 0.0004 |
| Model 1 | 1.54 (1.05-2.22) | 0.03 | 1.75 (1.28-2.36) | 0.0007 |
| Model 2 | 1.60 (1.06-2.38) | 0.03 | 1.74 (1.26-2.36) | 0.001 |
| Model 3 | 1.67 (1.08-2.57) | 0.02 | 1.79 (1.28-2.47) | 0.0009 |
| Plasma NT-proBNP* | | | | |
| Unadjusted | 1.24 (0.83-1.85) | NS | 1.21 (0.92-1.60) | NS |
| Model 1 | 1.26 (0.83-1.87) | NS | 1.22 (0.93-1.61) | NS |
| Model 2 | 1.30 (0.85-1.98) | NS | 1.22 (0.91-1.63) | NS |

*Ln transformed data (hazard ratio are per 1 log unit increase)
Model 1: Adjusted for age
Model 2: Adjusted for age and urine protein/creatinine ratio
Model 3: Adjusted for age, urine protein/creatinine ratio, and plasma NT-proBNP CV, cardiovascular; NT-CNP-53, N-terminal fragment of C-type natriuretic peptide-53; NT-proBNP, N-terminal pro-B-type natriuretic peptide; NS, not significant (i.e. p > 0.05).

TABLE 6

Measures of predictive accuracy.

| Model | C-index (95% CI) | Integrated discrimination improvement, % (SE) | p-value |
|---|---|---|---|
| Death | | | |
| NT-proBNP† | 0.57 (0.43-0.71) | — | — |
| NT-CNP-53‡ | 0.66 (0.53-0.78) | — | — |
| NT-proBNP† and NT-CNP-53‡ | 0.69 (0.56-0.82) | 30 (11)* | 0.004* |

TABLE 6-continued

Measures of predictive accuracy.

| Model | C-index (95% CI) | Integrated discrimination improvement, % (SE) | p-value |
|---|---|---|---|
| Death/rehospitalization | | | |
| NT-proBNP[†] | 0.56 (0.46-0.66) | — | — |
| NT-CNP-53[‡] | 0.67 (0.59-0.76) | — | |
| NT-proBNP[†] and NT-CNP-53[‡] | 0.69 (0.61-0.78) | 17 (5.0)* | 0.001* |

[†]Plasma NT-proBNP
[‡]Urinary NT-CNP-53
*compared to NT-proBNP alone
NT-proBNP, N-terminal pro-B type natriuretic peptide;
NT-CNP-53, N-terminal fragment of C-type natriuretic peptide -53;
SE, standard error.

These results demonstrate that elevated KIM-1 excretion appears to discriminate between decompensated heart failure patients and healthy control patients, but does not correlate with heart failure outcome. By contrast, elevated urinary NT-CNP-53 excretion demonstrated a significant correlation with adverse outcome within a heterogeneous hospitalized heart failure population (e.g., ADHF patients), independent of GFR. NT-CNP-53 was the only urinary biomarker with predictive value.

Example 3—Plasma CNP-22 is an Endothelial Cell Biomarker that Predicts Mortality and Myocardial Infarction in the General Population The following was performed to determine if plasma CNP-22 is an endothelial cell derived biomarker for predicting future mortality and myocardial infarction (MI) in the general population. Plasma CNP-22 was assessed in 1,841 subjects (mean age 62±11 years, 48% male) randomly selected from the general community of Olmsted County, Minn., USA. Median follow-up for mortality and MI was 12 years. Over the 12 year follow-up period, elevated plasma CNP-22 (CNP-22>16 pg/mL) was significantly associated with mortality (unadjusted HR 1.41, 95% CI 1.12-1.79; P=0.004) and MI (unadjusted HR 1.60, 95% CI 1.19-2.16; P=0.002) (Table 7). After adjusting for traditional risk factors (e.g., age, gender, body mass index (BMI), cholesterol, serum creatinine, smoking, and presence of diabetes and hypertension), elevated plasma CNP-22 levels remained significantly associated with mortality (adjusted HR 1.34, 95% CI 1.02-1.75; P=0.04) and MI (adjusted HR 1.59, 95% CI 1.13-2.25; P=0.008) (Table 7).

TABLE 7

Elevated plasma CNP-22 levels predict mortality and cardiovascular morbidity (overall cohort; n = 1841).

| | HR (95% CI) | |
|---|---|---|
| Outcome | Log CNP-22 | p Value |
| Death (n = 328) | | |
| Unadjusted | 1.414 (1.115-1.793) | 0.0043 |
| Age, Sex, BMI | 1.326 (1.016-1.730) | 0.0380 |
| Model 3 | 1.336 (1.019-1.752) | 0.0362 |
| MI (n = 189) | | |
| Unadjusted | 1.602 (1.187-2.161) | 0.0021 |
| Age, Sex, BMI | 1.699 (1.219-2.369) | 0.0018 |
| Model 3 | 1.591 (1.128-2.245) | 0.0082 |

Model 3: age, sex, BMI, total cholesterol, serum creatinine, smoking, presence of diabetes, hypertension, coronary artery disease Death and MI according to quartiles of plasma CNP-22 are shown in FIGS. 15A and 15B, respectively. The unadjusted incidence of death and MI events significantly increased with increasing quartiles of plasma CNP-22, where CNP-22 Q1=2.0 to 10.1 pg/mL; CNP-22 Q2=10.2 to 13.1 pg/mL; CNP-22 Q3=13.2 to 16.7 pg/mL; and CNP-22 Q4=16.8 to 265.0 pg/mL.

These results demonstrate that an elevated plasma CNP-22 level is an endothelial cell biomarker that can predict future cardiac-related death and MI in the general community. These results also demonstrate that humans with elevated plasma CNP-22 levels can be subjected to early MI detection strategies and/or aggressive therapeutic strategies for MI prevention.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating a mammal having an increased risk of acute decompensated heart failure, wherein said method comprises:
   (a) determining that said mammal has an elevated level of urinary NT-CNP-53,
   (b) monitoring said mammal for the presence of a risk factor for said acute decompensated heart failure, and
   (c) administering an ACE inhibitor, an angiotensin receptor blocker, an aldosterone antagonist, a statin, a native natriuretic peptide, or a designer natriuretic peptide to said mammal.

2. The method of claim 1, wherein said mammal is a human.

3. The method of claim 1, wherein said elevated level is greater than 36,000 pg of NT-CNP-53/day.

4. The method of claim 1, wherein said elevated level is greater than 42,000 pg of NT-CNP-53/day.

5. The method of claim 1, wherein said risk factor is selected from the group consisting of an age factor, hypertension, an elevated serum creatinine level, proteinuria, an elevated body mass index, an elevated cholesterol level, a smoking habit, and diabetes.

6. The method of claim 1, wherein said method comprises administering said angiotensin receptor blocker to said mammal.

* * * * *

SEQUENCE LISTING

```
<160> NUMBER OF SEQ ID NOS: 6

<210> SEQ ID NO 1
<211> LENGTH: 103
<212> TYPE: PRT
<213> ORGANISM: Homo sapiens

<400> SEQUENCE: 1

Lys Pro Gly Ala Pro Pro Lys Val Pro Arg Thr Pro Pro Ala Glu Glu
1               5                   10                  15

Leu Ala Glu Pro Gln Ala Ala Gly Gly Gly Gln Lys Lys Gly Asp Lys
            20                  25                  30
```

Ala Pro Gly Gly Gly Ala Asn Leu Lys Gly Asp Arg Ser Arg Leu
            35                  40                  45

Leu Arg Asp Leu Arg Val Asp Thr Lys Ser Arg Ala Ala Trp Ala Arg
 50                  55                  60

Leu Leu Gln Glu His Pro Asn Ala Arg Lys Tyr Lys Gly Ala Asn Lys
 65                  70                  75                  80

Lys Gly Leu Ser Lys Gly Cys Phe Gly Leu Lys Leu Asp Arg Ile Gly
                85                  90                  95

Ser Met Ser Gly Leu Gly Cys
            100

<210> SEQ ID NO 2
<211> LENGTH: 50
<212> TYPE: PRT
<213> ORGANISM: Homo sapiens

<400> SEQUENCE: 2

Lys Pro Gly Ala Pro Lys Val Pro Arg Thr Pro Pro Ala Glu Glu
 1               5                  10                  15

Leu Ala Glu Pro Gln Ala Ala Gly Gly Gln Lys Lys Gly Asp Lys
                20                  25                  30

Ala Pro Gly Gly Gly Ala Asn Leu Lys Gly Asp Arg Ser Arg Leu
            35                  40                  45

Leu Arg
 50

<210> SEQ ID NO 3
<211> LENGTH: 53
<212> TYPE: PRT
<213> ORGANISM: Homo sapiens

<400> SEQUENCE: 3

Asp Leu Arg Val Asp Thr Lys Ser Arg Ala Ala Trp Ala Arg Leu Leu
 1               5                  10                  15

Gln Glu His Pro Asn Ala Arg Lys Tyr Lys Gly Ala Asn Lys Lys Gly
                20                  25                  30

Leu Ser Lys Gly Cys Phe Gly Leu Lys Leu Asp Arg Ile Gly Ser Met
            35                  40                  45

Ser Gly Leu Gly Cys
 50

<210> SEQ ID NO 4
<211> LENGTH: 31
<212> TYPE: PRT
<213> ORGANISM: Homo sapiens

<400> SEQUENCE: 4

Asp Leu Arg Val Asp Thr Lys Ser Arg Ala Ala Trp Ala Arg Leu Leu
 1               5                  10                  15

Gln Glu His Pro Asn Ala Arg Lys Tyr Lys Gly Ala Asn Lys Lys
                20                  25                  30

<210> SEQ ID NO 5
<211> LENGTH: 22
<212> TYPE: PRT
<213> ORGANISM: Homo sapiens

<400> SEQUENCE: 5

Gly Leu Ser Lys Gly Cys Phe Gly Leu Lys Leu Asp Arg Ile Gly Ser
 1               5                  10                  15

```
Met Ser Gly Leu Gly Cys
                20

<210> SEQ ID NO 6
<211> LENGTH: 81
<212> TYPE: PRT
<213> ORGANISM: Homo sapiens

<400> SEQUENCE: 6

Lys Pro Gly Ala Pro Pro Lys Val Pro Arg Thr Pro Pro Ala Glu Glu
1               5                   10                  15

Leu Ala Glu Pro Gln Ala Ala Gly Gly Gly Gln Lys Lys Gly Asp Lys
                20                  25                  30

Ala Pro Gly Gly Gly Ala Asn Leu Lys Gly Asp Arg Ser Arg Leu
            35                  40                  45

Leu Arg Asp Leu Arg Val Asp Thr Lys Ser Arg Ala Ala Trp Ala Arg
    50                  55                  60

Leu Leu Gln Glu His Pro Asn Ala Arg Lys Tyr Lys Gly Ala Asn Lys
65                  70                  75                  80

Lys
```